(12) United States Patent
Lee et al.

(10) Patent No.: US 7,629,145 B2
(45) Date of Patent: Dec. 8, 2009

(54) VEGF-RELATED PROTEIN

(75) Inventors: James Lee, San Bruno, CA (US); William Wood, Cupertino, CA (US)

(73) Assignee: Genentech, Inc., South San Francisco, CA (US)

(*) Notice: Subject to any disclaimer, the term of this patent is extended or adjusted under 35 U.S.C. 154(b) by 232 days.

(21) Appl. No.: 11/427,463

(22) Filed: Jun. 29, 2006

(65) Prior Publication Data

US 2007/0036813 A1 Feb. 15, 2007

Related U.S. Application Data

(62) Division of application No. 10/346,802, filed on Jan. 17, 2003, now abandoned, which is a division of application No. 09/313,299, filed on May 17, 1999, now Pat. No. 6,576,608, which is a division of application No. 08/706,054, filed on Aug. 30, 1996, now Pat. No. 6,451,764.

(60) Provisional application No. 60/003,491, filed on Sep. 8, 1995.

(51) Int. Cl.
  C12P 21/02 (2006.01)
  C12N 15/03 (2006.01)
  C12N 15/09 (2006.01)
  C07H 21/04 (2006.01)

(52) U.S. Cl. .............. 435/69.1; 435/252.33; 435/320.1; 536/23.5

(58) Field of Classification Search ................ 536/23.5; 435/252.3
See application file for complete search history.

(56) References Cited

U.S. PATENT DOCUMENTS

| | | | |
|---|---|---|---|
| 5,185,438 A | 2/1993 | Lemischka | |
| 5,194,596 A | 3/1993 | Tischer et al. | |
| 5,219,739 A | 6/1993 | Tischer et al. | |
| 5,283,354 A | 2/1994 | Lemischka | |
| 5,326,695 A | 7/1994 | Andersson et al. | |
| 5,607,918 A | 3/1997 | Eriksson et al. | |
| 5,776,755 A | 7/1998 | Alitalo et al. | |
| 5,932,540 A | 8/1999 | Hu et al. | |
| 5,935,820 A | 8/1999 | Hu et al. | |
| 6,040,157 A | 3/2000 | Hu et al. | |
| 6,107,046 A | 8/2000 | Alitalo et al. | |
| 6,130,071 A | 10/2000 | Alitalo et al. | |
| 6,221,839 B1 * | 4/2001 | Alitalo et al. | 514/12 |
| 6,245,530 B1 | 6/2001 | Alitalo et al. | |
| 6,361,946 B1 | 3/2002 | Alitalo et al. | |
| 6,403,088 B1 | 6/2002 | Alitalo et al. | |
| 6,451,764 B1 | 9/2002 | Lee et al. | |
| 6,608,182 B1 | 8/2003 | Rosen et al. | |
| 6,645,933 B1 | 11/2003 | Alitalo et al. | |
| 6,730,658 B1 | 5/2004 | Alitalo et al. | |
| 6,734,285 B2 | 5/2004 | Hu et al. | |
| 6,818,220 B1 | 11/2004 | Alitalo et al. | |
| 6,824,777 B1 | 11/2004 | Alitalo et al. | |
| 6,828,426 B1 | 12/2004 | Hirata et al. | |
| 6,994,989 B1 | 2/2006 | Lyman | |
| 7,034,105 B2 | 4/2006 | Alitalo et al. | |
| 7,109,308 B1 | 9/2006 | Rosen et al. | |
| 7,115,392 B2 | 10/2006 | Rosen et al. | |
| 7,125,714 B2 | 10/2006 | Alitalo et al. | |
| 7,153,827 B1 | 12/2006 | Hu et al. | |
| 7,153,942 B2 | 12/2006 | Hu et al. | |
| 7,186,688 B1 | 3/2007 | Hu et al. | |
| 7,227,005 B1 | 5/2007 | Hu et al. | |
| 7,423,125 B2 | 9/2008 | Alitalo et al. | |
| 7,429,333 B2 | 9/2008 | Chiou et al. | |
| 7,498,417 B2 | 3/2009 | Hu et al. | |
| 2002/0120123 A1 | 8/2002 | Rosen et al. | |
| 2002/0182683 A1 | 12/2002 | Hu et al. | |
| 2003/0008357 A1 | 1/2003 | Hu et al. | |
| 2003/0028007 A1 | 2/2003 | Hu et al. | |
| 2003/0091567 A1 | 5/2003 | Alitalo et al. | |
| 2004/0037820 A1 | 2/2004 | Alitalo et al. | |
| 2004/0143103 A1 | 7/2004 | Hu et al. | |
| 2004/0147448 A1 | 7/2004 | Alitalo et al. | |
| 2004/0147726 A1 | 7/2004 | Alitalo | |

(Continued)

FOREIGN PATENT DOCUMENTS

DE 1974/8734 A1 5/1999

(Continued)

OTHER PUBLICATIONS

Aprelikova et al., "FLT4, a Novel Class III Receptor Tyrosine Kinase in Chromosome 5q33-gter[1]" *Cancer Research* 52:746-748 (1992).
Aviv et al., "Purification of Biologically Active Globin Messenger RNA by Chromatography on Oligothymidylic Acid-Cellulose" *Proc. Natl. Acad. Sci. USA* 69(6):1408-1412 (Jun. 1972).
Bennett et al., "Cloning and Characterization of HTK, a Novel Transmembrane Tyrosine Kinase of the EPH Subfamily" *Journal of Biological Chemistry* 269(19):14211-14218 (1994).
Bennett et al., "Extracellular Domain-IgG Fusion Proteins for Three Human Natriuretic Peptide Receptors. Hormone Pharmacology and Application to Solid Phase Screening of Synthetic Antisera" *The Journal of Biological Chemistry* 266(34):23060-23067 (1991).
Borg et al., "Biochemical characterization of two isoforms of FLT4, a VEGF receptor-related tyrosine kinase" *Oncogene* 10:973-984 (1995).

(Continued)

*Primary Examiner*—Phuong Huynh
(74) *Attorney, Agent, or Firm*—Ashe, P.C.

(57) ABSTRACT

A human VEGF-related protein (VRP) has been identified and isolated that binds to, and stimulates the phosphorylation of, the receptor tyrosine kinase Flt4. The VRP is postulated to be a third member of the VEGF protein family. Also provided are antibodies that bind to VRP and neutralize a biological activity of VRP, compositions containing the VRP or antibody, methods of use, chimeric polypeptides, and a signal polypeptide for VRP.

9 Claims, 10 Drawing Sheets

U.S. PATENT DOCUMENTS

| | | | |
|---|---|---|---|
| 2004/0208879 | A1 | 10/2004 | Alitalo et al. |
| 2004/0213790 | A1 | 10/2004 | Lee et al. |
| 2004/0214286 | A1 | 10/2004 | Hu et al. |
| 2005/0176103 | A1 | 8/2005 | Hu et al. |
| 2005/0256050 | A1 | 11/2005 | Hu et al. |
| 2005/0287143 | A1 | 12/2005 | Rosen et al. |
| 2006/0014252 | A1 | 1/2006 | Lyman |
| 2006/0025331 | A1 | 2/2006 | Hu et al. |
| 2006/0177901 | A1 | 8/2006 | Alitalo et al. |
| 2008/0241152 | A1 | 10/2008 | Alitalo et al. |
| 2008/0241153 | A1 | 10/2008 | Alitalo et al. |
| 2009/0104198 | A1 | 4/2009 | Alitalo et al. |

FOREIGN PATENT DOCUMENTS

| | | |
|---|---|---|
| EP | 0506477 B1 | 9/1992 |
| WO | WO 90/13649 | 11/1990 |
| WO | WO 92/14748 | 9/1992 |
| WO | WO 93/15201 | 8/1993 |
| WO | WO 94/01576 | 1/1994 |
| WO | WO 94/10202 | 5/1994 |
| WO | WO 94/11499 | 5/1994 |
| WO | WO 95/09656 | 4/1995 |
| WO | WO 95/21613 | 8/1995 |
| WO | WO 95/21865 | 8/1995 |
| WO | WO 95/21868 | 8/1995 |
| WO | WO 95/24473 | 9/1995 |
| WO | WO 95/33772 | 12/1995 |
| WO | 96/27007 | 9/1996 |
| WO | WO 96/26736 | 9/1996 |
| WO | WO 96/39421 | 12/1996 |
| WO | WO 96/39515 | 12/1996 |
| WO | WO 97/05250 | 2/1997 |
| WO | WO 97/09427 | 3/1997 |
| WO | WO 97/12972 | 4/1997 |
| WO | WO 97/17442 | 5/1997 |
| WO | WO 98/07832 | 2/1998 |
| WO | WO 98/24811 | 6/1998 |
| WO | WO 98/33917 | 8/1998 |
| WO | WO 98/49300 | 11/1998 |
| WO | WO 99/46364 | 9/1999 |
| WO | WO 00/21560 | 4/2000 |
| WO | WO 02/060950 | 8/2002 |

OTHER PUBLICATIONS

Cathala et al., "Laboratory Methods. A Method for Isolation of Intact, Translationally Active Ribonucleic Acid" *DNA* 2(4):329-335 (1983).
de Vries et al., "The fms-like tyrosine kinase, a receptor for vascular endothelial growth factor" *Science* 255:989-991 (1992).
Dermer, G., "Another anniversary for the war on cancer" *Biotechnology* 12:320 (1994).
Ferrara et al., "Molecular and biological properties of the vascular endothelial growth factor family of proteins" *Endo. Rev.* 13(1):18-32 (Feb. 1992).
Ferrara et al., "The vascular endothelial growth factor family of polypeptides" *J. Cell. Biochem.* 47:211-218 (1991).
Ferrara, N., "Molecular and biological properties of vascular endothelial growth factor" *J Mol Med* 77:527-543 (1999).
Finnerty et al., "Molecular Cloning of Murine FLT and FLT4" *Oncogene* 8:2293-2298 (1993).
Folkman and Klagsbrun, "Angiogenic factors" *Science* 235:442-447 (1987).
Folkman and Shing, "Angiogenesis" *Journal of Biological Chemistry* 267:10931-10934 (1992).
Folkman., "Angiogenesis in Cancer, Vascular, Rheumatoid and Other Disease." *Nature Medicine.* 1(1):27-31 (1995).
Fong et al., "Role of the Flt-1 receptor tyrosine kinase in regulating the assembly of vascular endothelium" *Nature* 376:66-70 (Jul. 6, 1995).
Galland et al., "Chromosomal Localization of FLT4, a Novel Receptor-Type Tyrosine Kinase Gene" *Genomics* 13:475-478 (1992).

Galland et al., "The FLT4 Gene Encodes a Transmembrane Tyrosine Kinase Related to the Vascular Endothelial Growth Factor Receptor" *Oncogene* 8:1233-1240 (1993).
GenBank Accession No. N42368, record created Jan. 25, 1996.
GenBank Accession No. N42374, record created Jan. 25, 1996.
GenBank Accession No. U43142, record created Jan. 9, 1996.
GenBank Accession No. X94216, record created Feb. 6, 1996.
GenBank Accession No. Z44272, record created Nov. 14, 1994.
Godowski et al., "Reevaluation of the Roles of Protein S and Gas6 as Ligands for the Receptor Tyrosine Kinase Rse/Tyro 3" *Cell* 82:355-358 (Aug. 11, 1995).
Grimmond et al., "Cloning and Characterization of a Novel Human Gene Related to Vascular Endothelial Growth Factor" *Genome Research* 6:124-131 (1996).
Gura, T., "Systems for identifying new drugs are often faulty" *Science* 278(5340):1041-1042 (Nov. 7, 1997).
Hamel et al., "Neurotrophin gene expression by cell lines derived from human gliomas" *J. Neurosci. Res.* 34:147-157 (1993).
Hatva et al., "Expression of endothelial cell-specific receptor tyrosine kinases and growth factors in human brain tumors" *Am. J. Pathol.* 146:368-378 (1995).
Hauser and Weich, "A heparin-binding form of placenta growth factor (PlGF-2) is expressed in human umbilical vein endothelial cells and in placenta" *Growth Factors* 9:259-268 (1993).
Holmes et al., "Structure and Functional Expression of a Human Interleukin-8 Receptor" *Science* 253(5025):1278-1280 (1991).
Houck et al., "The Vascular Endothelial Growth Factor Family: Identification of a Fourth Molecular Species and Characterization of Alternative Splicing of RNA" *Mol. Endocrinol.* 5(12):1806-1814 (Dec. 1991).
Imbert et al., "Characterization of a yeast artificial chromosome from human chromosome band 13q12 containing the FLT1 and FLT3 receptor-type tyrosine kinase genes" *Cytogenet. Cell. Genet.* 67(175-177):175-177 (1994).
Joukov et al, "Proteolytic processing regulates receptor specificity and activity of VEGF-C" *ENBO J.* 16(13):3898-3911 (Jul. 1, 1997).
Joukov et al., "A novel vascular endothelial growth factor, VEGF-C, is a ligand for the Flt4 (VEGFR-3) and KDR (VEGF-2) receptor tyrosine kinases" *EMBO Journal* 15:1751 (1996).
Joukov, V. et al., "A Novel Vascular Endothelial Growth Factor, VEGF-C, is a Ligand for the Flt4 (VEGFR-3) and KDR (VEGFR-2) Receptor Tyrosine Kinases" *EMBO Journal* 15(2):290-298 (1996).
Kaipainen et al., "Expression of the fms-like tyrosine kinase 4 gene becomes restricted to lymphatic endothelium during development" *Proc. Natl. Acad. Sci.* 92:3566-3570 (1995).
Kaipainen et al., "The Related FLT4, FLT1 and KDR Receptor Tyrosine Kinases Show Distinct Expression Patterns in Human Fetal Endothelial Cells" *Journal of Experimental Medicine* 178:2077-2088 (1993).
Klagsbrun and D'Amore, "Regulators of angiogenesis" *Ann. Rev. Physiol.* 53:217-239 (1991).
Kozak, M., "Compilation and analysis of sequences upstream from the translational start site in eukaryotic mRNAs" *Nucl. Acids. Res.* 12:857-872 (1984).
Lasky et al., "DNA sequence analysis of the type-common glycoprotein-D genes of herpes simplex virus types 1 and 2" *DNA* 3(1):23-29 (1984).
Lee, J. et al., "Vascular Endothelial Growth Factor-Related Protein: A Ligand and Specific Activator of the Tyrosine Kinase Receptor Flt4" *Proc. Natl. Acad. Sci.* 93:1988-1992 (1996).
Lyttle, D. et al., "Homologs of vascular endothelial growth factor are encoded by the poxvirus orf virus" *Journal of Virology* 68(1):84-92 (Jan. 1994).
Maglione et al., "Isolation of a human placenta cDNA coding for a protein related to the vascular permeability factor" *Proc. Natl. Acad. Sci.* 88:9267-9271 (1991).
Maglione et al., "Two alternative mRNAs coding for the angioigenic factor, placenta growth factor (PlGF), are transcribed from a single gene of chromosome 14" *Oncogene* 8:925-931 (1993).
Matthews et al., "A Receptor Tyrosine Kinase cDNA Isolated from a Population of Enriched Primitive Hematopoietic Cells and Exhibiting Close Genetic Linkage to c-kit." *Proc. Natl. Acad. Sci.* 88:9026-9030 (1991).

Millauer et al., "High affinity VEGF binding and developmental expression suggest Flk-1 as a major regulator of vasculogenesis and angiogenesis" *Cell* 72:835-846 (1993).

Miller et al., "Vascular endothelial growth factor/vascular permeability factor is temporally and spatially correlated with ocular angiogenesis in a primate model" *Am. J. Pathol.* 145:574-584 (1994).

Mustonen and Alitalo, "Endothelial receptor tyrosine kinases involved in angiogenesis" *Journal of Cell Biology* 129:895-898 (1995).

Neufeld et al., "Vascular endothelial growth factor and its receptors" *Progress in Growth Factor Research* 5(1):89-97 (1994).

Ngo, et al., "Computational Complexity, Protein Structure Prediction, and the Levinthal Paradox" *The Protein Folding Problem and Tertiary Structure Prediction* pp. 491-495 (1994).

Oelrichs et al., "NYK/FLK-1: a putative receptor protein tyrosine kinase isolated from E10 embryonic neuroepithelium is expressed in endothelial cells of the developing embryo" *Oncogene* 8:11-18 (1993).

Olofsson et al., "Vascular endothelial growth factor B, a novel growth factor for endothelial cells" *Proc. Natl. Acad. Sci. USA* 93:2576-2581 (1996).

Pajusola et al., "FLT4 Receptor Tyrosine Kinase Contains Seven Immunoglobulin like loops and is Expressed in Multiple Human Tissues and Cell Lines" *Cancer Research* 52:5738-5743 (1992).

Pajusola et al., "Signalling properties of FLT4, a proteolytically processed receptor tyrosine kinase related to two VEGF receptors" *Oncogene* 9:3545-3555 (1994).

Pajusola et al., "Two Human FLT4 Receptor Tyrosine Kinase Isoforms with Distinct Carboxy Terminal Tails are Produced by Alternative Processing of Primary Transcripts" *Oncogene* 8:2931-2937 (1993).

Park et al., "Placenta growth factor. Potentiation of vascular endothelial growth factor bioactivity, in vitro and in vivo, and high affinity binding to Flt-1 but not to Flk-1/KDR" *Journal of Biological Chemistry* 269(41):25646-25654 (1994).

Paulsson et al., "The Balbiani ring 3 gene in *Chironomus tentans* has a diverged repetitive structure split by many introns" *J. Mol. Biol.* 211:331-349 (1990).

Pennica et al., "Expression cloning of cardiotrophin 1, a cytokine that induces cardiac myocyte hypertrophy" *Proc. Natl. Acad. Sci. USA* 92:1142-1146 (1995).

Perlman and Halvorson, "A putative signal peptidase recognition site and sequence in eukaryotic and prokaryotic signal peptides" *J. Mol. Biol.* 167:391-409 (1983).

Quinn et al., "Fetal liver kinase 1 is a receptor for vascular endothelial growth factor and is selectively expressed in vascular endothelium" *Proc. Natl. Acad. Sci.* 90:7533-7537 (1993).

Reynolds et al., "Angiogenesis in the female reproductive system" *FASEB J.* 6:886-892 (1992).

Risau et al., "Vasculogenesis and angiogenesis in embryonic-stem-cell-derived embryoid bodies" *Development* 102:471-478 (1988).

Sait et al., "The kinase insert domain receptor gene (KDR) has been relocated to chromosome 4q11—>q12" *Cytogenet. Cell. Genet.* 70:145-146 (1995).

Sarazani et al., "A Novel Endothelial Tyrosine Kinase cDNA Homologous to Platelet-Derived Growth Factor Receptor cDNA" *Biochem. & Biophys. Res. Comm.* 186:706-714 (1992).

Shalaby et al., "Failure of blood-island formation and vasculogenesis in Flk-1-deficient mice" *Nature* 376:62-66 (1995).

Shibuya et al., "Nucleotide Sequence and Expression of a Novel Human Receptor-Type Tyrosine Kinase Gene (flt) Closely Related to the fms Family." *Oncogene* 5:519-524 (1990).

Spritz et al., "A YAC contig spanning a cluster of human type III receptor protein tyrosine kinase genes (PDGFRA-KIT-KDR) in chromosome segment 4q12" *Genomics* 22:431-436 (1994).

Stryer et al. *Biochemistry*, Third edition, New York:W H Freeman Company pp. 31-33 (1988).

Suva et al., "A parathyroid hormone-related protein implicated in malignant hypercalcemia: cloning and expression" *Science* 237(4817):893-896 (Aug. 1987).

Terman et al., "Identification of a New Endothelial Cell Growth Factor Receptor Tyrosine Kinase." *Oncogene.* 6:1677-1683 (1991).

Terman et al., "Identification of the KDR Tyrosine Kinase as a Receptor for Vascular Endothelial Cell Growth Factor." *Biochem. & Biophys. Res. Comm.* 187:1579-1586 (1992).

Voet et al, "Chemical Evolution and Abnormal Hemoglobin" *John Wiley & Sons* (Section 6-3 and Section 9-3) pp. 126-128 and 228-234 (1990).

von Heijne, G., "A new method for predicting signal sequence cleavage sites" *Nucleic Acids Research* 14:4683-4690 (1986).

Wilks, "Two putative protein-tyrosine kinases identified by application of the polymerase chain reaction" *Proc. Natl. Acad. Sci. USA* 86:1603-1607 (1989).

Yamaguchi et al., "flk-1, an flt-related receptor tyrosine kinase is an early marker for endothelial cell precursors" *Development* 118:489-498 (1993).

Amino Acid sequence alignment of Genentech VRP Protein and amino acid sequences disclosed in Human Genome Sciences patent applications, EP0751992(D1) and EP0837934(D3) submitted on Nov. 3, 2004 in connection with European Patent No. 848755.

ATCC Deposit for deposit No. 97231 deposited on Jul. 24, 1995 submitted in connection with European Patent No. 848755.

Declaration 2 of Peter Robert Schofield dated Dec. 16, 2002 submitted in connection with Australian Patent No. 710696.

Declaration of Brandon John Wainwright dated Apr. 23, 2001 submitted in connection with Australian Patent No. 710696.

Declaration of Dr. Aaronson dated Sep. 14, 2007 submitted in connection with European Patent No. 848755.

Declaration of Dr. Aaronson dated Nov. 22, 2006 submitted in connection with European Patent No. 848755.

Declaration of Dr. Gil Choi dated Feb. 27, 2004 submitted in connection with European Patent No. 848755.

Declaration of Dr. John J. Chicca dated Nov. 22, 2006 submitted in connection with European Patent 848755.

Declaration of Dr. Skobe dated Nov. 22, 2006 submitted in connection with European Patent No. 848755.

Declaration of Francis John Ballard dated Feb. 16, 2004 submitted in connection with Australian Patent No. 710696.

Declaration of Francis John Ballard dated Oct. 26, 2000 submitted in connection with Australian Patent 710696.

Declaration of Gary Baxter Cox dated Apr. 26, 2001 submitted in connection with Australian Patent No. 710696.

Declaration of Ian Jeffrey Rourke dated Dec. 3, 2007 submitted in connection with Australian Patent No. 710696.

Declaration of John Francis McCann dated Jun. 26, 2000 submitted in connection with Australian Patent No. 710696.

Declaration of Kari Alitalo dated Sep. 15, 2003 submitted in connection with Australian Patent No. 710696.

Declaration of Kari Alitalo dated Sep. 15, 2003 submitted in connection with European Patent No. 848755.

Declaration of Nicholas Johannes Hoogenraad dated Jun. 2, 2008 submitted in connection with Australian Patent No. 710696.

Declaration of Peter Adrian Walton Rogers dated Feb. 13, 2004 submitted in connection with Australian Patent No. 710696.

Declaration of Peter Adrian Walton Rogers dated Oct. 26, 2000 submitted in connection with Australian Patent No. 710696.

Declaration of Peter J. Hudson dated Jun. 3, 2008 submitted in connection with Australian Patent No. 710696.

Declaration of Peter Philip Gray dated Dec. 17, 2002 submitted in connection with Australian Patent No. 710696.

Declaration of Peter Philip Gray dated Oct. 17, 2002 submitted in connection with Australian Patent No. 710696.

Declaration of Peter Robert Schofield dated Dec. 16, 2002 submitted in connection with Australian Patent No. 710696.

Declaration of Piroska Elizabeth Rakoczy dated Apr. 16, 2004 submitted in connection with Australian Patent No. 710696.

Declaration of Piroska Elizabeth Rakoczy dated Apr. 24, 2001 submitted in connection with Australian Patent No. 710696.

File inspection results relating to Human Genome Sciences PCT Application PCT/US94/05291 submitted on Nov. 15, 2007 in connection with European Patent No. 848755.

Letter from John J. Chicca II, Ph.D., Molecular Diagnostic Services, Inc. regarding a third progress report for a project entitled "Cloning and expression of VEGF-2 gene and the efficacy of VEGF-2 protein utilizing the 3-D collagen angiogenesis assay and proliferation," dated Feb. 16, 2006.

Petition of Jan. 10, 2003 submitted by Human Genome Sciences, Inc. In connection with European Patent No. 848755.

Witness statement of Professor Vincenzo Cerundolo dated Nov. 24, 2006 submitted in connection with European Patent No. 846755.

* cited by examiner

```
  1 CGCGGGGTGT TCTGGTGTCC CCCGCCCCGC CTCTCCAAAA AGCTACACCG ACGCGGACCG
    GCGCCCCACA AGACCACAGG GGGCGGGGCG AGAGGTTTT TCGATGTGGC TGCGCCTGGC sstI
 61 CGGCGGCGTC CTCCCTCGCC CTCGCTTCAC CTCGCGGGCT CCGAATGCGG GGAGCTCGGA
    GCCGCCGCAG GAGGGAGCGG GAGCGAAGTG GAGCGCCCGA GGCTTACGCC CCTCGAGCCT 121 TGTCCGGTTT CCTGTGAGGC TTTTACCTGA CACCCGCCGC CTTTCCCCGG CACTGGCTGG
    ACAGGCCAAA GGACACTCCG AAAATGGACT GTGGGCGGCG AAAGGGGCC GTGACCGACC kasI
181 GAGGGCGCCC TGCAAAGTTG GGAACGCGGA GCCCCGGACC CGCTCCCGCC GCCTCCGGCT
    CTCCCGCGGG ACGTTTCAAC CCTTGCGCCT CGGGGCCTGG GCGAGGGCGG CGGAGGCCGA 241 CGCCCAGGGG GGGTCGCCGG GAGGAGCCCG GGGGAGAGGG ACCAGGAGGG GCCCGCGGCC
    GCGGGTCCCC CCCAGCGGCC CTCCTCGGGC CCCCTCTCCC TGGTCCTCCC CGGGCGCCGG kasI                                          ageI
301 TCGCAGGGGC GCCCGCGCCC CCACCCCTGC CCCCGCCAGC GGACCGGTCC CCCACCCCCG
    AGCGTCCCCG CGGGCGCGGG GGTGGGGACG GGGGCGGTCG CCTGGCCAGG GGGTGGGGGC 361 GTCCTTCCAC CATGCACTTG CTGGGCTTCT TCTCTGTGGC GTGTTCTCTG CTCGCCGCTG
    CAGGAAGGTG GTACGTGAAC GACCCGAAGA AGAGACACCG CACAAGAGAC GAGCGGCGAC
-20         M  H  L  L  G  F  F  S  V  A  C  S  L  L  A  A  A kasI
421 CGCTGCTCCC GGGTCCTCGC GAGGCGCCCG CCGCCGCCGC CGCCTTCGAG TCCGGACTCG
    GCGACGAGGG CCCAGGAGCG CTCCGCGGGC GGCGGCGGCG GCGGAAGCTC AGGCCTGAGC
 -3   L  L  P  G  P  R  E  A  P  A  A  A  A  F  E  S  G  L  D 481 ACCTCTCGGA CGCGGAGCCC GACGCGGGCG AGGCCACGGC TTATGCAAGC AAAGATCTGG
    TGGAGAGCCT GCGCCTCGGG CTGCGCCCGC TCCGGTGCCG AATACGTTCG TTTCTAGACC
 18   L  S  D  A  E  P  D  A  G  E  A  T  A  Y  A  S  K  D  L  E 541 AGGAGCAGTT ACGGTCTGTG TCCAGTGTAG ATGAACTCAT GACTGTACTC TACCCAGAAT
    TCCTCGTCAA TGCCAGACAC AGGTCACATC TACTTGAGTA CTGACATGAG ATGGGTCTTA
 38   E  Q  L  R  S  V  S  S  V  D  E  L  M  T  V  L  Y  P  E  Y
```

FIG. 1A

601 ATTGGAAAAT GTACAAGTGT CAGCTAAGGA AAGGAGGCTG GCAACATAAC AGAGAACAGG
    TAACCTTTTA CATGTTCACA GTCGATTCCT TTCCTCCGAC CGTTGTATTG TCTCTTGTCC
 58     W  K  M  Y  K  C   Q  L  R  K  G  G   W  Q  H  N  R   E  Q  A

661 CCAACCTCAA CTCAAGGACA GAAGAGACTA TAAAATTTGC TGCAGCACAT TATAATACAG
    GGTTGGAGTT GAGTTCCTGT CTTCTCTGAT ATTTTAAACG ACGTCGTGTA ATATTATGTC
 78     N  L  N  S  R  T   E  E  T  I  K  F   A  A  A  H  Y   N  T  E sphI
721 AGATCTTGAA AAGTATTGAT AATGAGTGGA GAAAGACTCA ATGCATGCCA CGGGAGGTGT
    TCTAGAACTT TTCATAACTA TTACTCACCT CTTTCTGAGT TACGTACGGT GCCCTCCACA
 98     I  L  K  S  I  D   N  E  W  R  K  T   Q  C  M  P  R   E  V  C 781 GTATAGATGT GGGGAAGGAG TTTGGAGTCG CGACAAACAC CTTCTTTAAA CCTCCATGTG
    CATATCTACA CCCCTTCCTC AAACCTCAGC GCTGTTTGTG GAAGAAATTT GGAGGTACAC
118     I  D  V  G  K  E   F  G  V  A  T  N   T  F  F  K  P   P  C  V accI
841 TGTCCGTCTA CAGATGTGGG GGTTGCTGCA ATAGTGAGGG GCTGCAGTGC ATGAACACCA
    ACAGGCAGAT GTCTACACCC CCAACGACGT TATCACTCCC CGACGTCACG TACTTGTGGT
138     S  V  Y  R  C  G   G  C  N  S  E  G   L  Q  C  M  N   T  S 901 GCACGAGCTA CCTCAGCAAG ACGTTATTTG AAATTACAGT GCCTCTCTCT CAAGGCCCCA
    CGTGCTCGAT GGAGTCGTTC TGCAATAAAC TTTAATGTCA CGGAGAGAGA GTTCCGGGGT
158     T  S  Y  L  S  K   T  L  F  E  I  T   V  P  L  S  Q   G  P  K 961 AACCAGTAAC AATCAGTTTT GCCAATCACA CTTCCTGCCG ATGCATGTCT AAACTGGATG
    TTGGTCATTG TTAGTCAAAA CGGTTAGTGT GAAGGACGGC TACGTACAGA TTTGACCTAC
178     P  V  T  I  S  F   A  N  H  T  S  C   R  C  M  S  K   L  D  V 1021 TTTACAGACA AGTTCATTCC ATTATTAGAC GTTCCCTGCC AGCAACACTA CCACAGTGTC
     AAATGTCTGT TCAAGTAAGG TAATAATCTG CAAGGGACGG TCGTTGTGAT GGTGTCACAG
198     Y  R  Q  V  H  S   I  I  R  R  S  L   P  A  T  L  P   Q  C  Q 1081 AGGCAGCGAA CAAGACCTGC CCCACCAATT ACATGTGGAA TAATCACATC TGCAGATGCC
     TCCGTCGCTT GTTCTGGACG GGGTGGTTAA TGTACACCTT ATTAGTGTAG ACGTCTACGG
218     A  A  N  K  T  C   P  T  N  Y  M  W   N  N  H  I  C   R  C  L

FIG. 1B

```
1141 TGGCTCAGGA AGATTTTATG TTTTCCTCGG ATGCTGGAGA TGACTCAACA GATGGATTCC
     ACCGAGTCCT TCTAAAATAC AAAAGGAGCC TACGACCTCT ACTGAGTTGT CTACCTAAGG
 238   A  Q  E   D  F  M   F  S  S   D  A  G   D  D  S   T  D  G  F  H

1201 ATGACATCTG TGGACCAAAC AAGGAGCTGG ATGAAGAGAC CTGTCAGTGT GTCTGCAGAG
     TACTGTAGAC ACCTGGTTTG TTCCTCGACC TACTTCTCTG GACAGTCACA CAGACGTCTC
 258   D  I  C   G  P  N   K  E  L   D  E  E   T  C  Q   C  V  C  R  A

1261 CGGGGCTTCG GCCTGCCAGC TGTGGACCCC ACAAAGAACT AGACAGAAAC TCATGCCAGT
     GCCCCGAAGC CGGACGGTCG ACACCTGGGG TGTTTCTTGA TCTGTCTTTG AGTACGGTCA
 278   G  L  R   P  A  S   C  G  P   H  K  E   L  D  R   N  S  C  Q  C

1321 GTGTCTGTAA AAACAAACTC TTCCCCAGCC AATGTGGGGC AACCGAGAA TTTGATGAAA
     CACAGACATT TTTGTTTGAG AAGGGGTCGG TTACACCCCG GTTGGCTCTT AAACTACTTT
 298   V  C  K   N  K  L   F  P  S   Q  C  G   A  N  R   E  F  D  E  N

1381 ACACATGCCA GTGTGTATGT AAAAGAACCT GCCCCAGAAA TCAACCCCTA ATCCTGGAA
     TGTGTACGGT CACACATACA TTTTCTTGGA CGGGGTCTTT AGTTGGGGAT TAGGACCTT
 318   T  C  Q   C  V  C   K  R  T   C  P  R   N  Q  P   L  N  P  G  K

1441 AATGTGCCTG TGAATGTACA GAAAGTCCAC AGAAATGCTT GTTAAAAGGA AGAAGTTCC
     TTACACGGAC ACTTACATGT CTTTCAGGTG TCTTTACGAA CAATTTTCCT TCTTCAAGG
 338   C  A  C   E  C  T   E  S  P   Q  K  C   L  L  K   G  K  K  F  H eaeI
1501 ACCACCAAAC ATGCAGCTGT TACAGACGGC CATGTACGAA CCGCCAGAAG GCTTGTGAGC
     TGGTGGTTTG TACGTCGACA ATGTCTGCCG GTACATGCTT GGCGGTCTTC CGAACACTCG
 358   H  Q  T   C  S  C   Y  R  R   P  C  T   N  R  Q   K  A  C  E  P 1561 CAGGATTTTC ATATAGTGAA GAAGTGTGTC GTTGTGTCCC TTCATATTGG AAAAGACCAC
     GTCCTAAAAG TATATCACTT CTTCACACAG CAACACAGGG AAGTATAACC TTTTCTGGTG
 378   G  F  S   Y  S  E   E  V  C   R  C  V   P  S  Y   W  K  R  P  Q claI
1621 AAATGAGCTA AGATTGTACT GTTTTCCAGT TCATCGATTT TCTATTATGG AAAACTGTGT
     TTTACTCGAT TCTAACATGA CAAAAGGTCA AGTAGCTAAA AGATAATACC TTTTGACACA
 398   M  S  O 1681 TGCCACAGTA GAACTGTCTG TGAACAGAGA GACCCTTGTG GGTCCATGCT AACAAAGACA
     ACGGTGTCAT CTTGACAGAC ACTTGTCTCT CTGGGAACAC CCAGGTACGA TTGTTTCTGT
```

FIG. 1C

```
                                                                        sstI
1741 AAAGTCTGTC TTTCCTGAAC CATGTGGATA ACTTTACAGA AATGGACTGG AGCTCATCTG
     TTTCAGACAG AAAGGACTTG GTACACCTAT TGAAATGTCT TTACCTGACC TCGAGTAGAC 1801 CAAAAGGCCT CTTGTAAAGA CTGGTTTTCT GCCAATGACC AAACAGCCAA GATTTTCCTC
     GTTTTCCGGA GAACATTTCT GACCAAAAGA CGGTTACTGG TTTGTCGGTT CTAAAAGGAG 1861 TTGTGATTTC TTTAAAAGAA TGACTATATA ATTTATTTCC ACTAAAAATA TTGTTTCTGC
     AACACTAAAG AAATTTTCTT ACTGATATAT TAAATAAAGG TGATTTTTAT AACAAAGACG 1921 ATTCATTTTT ATAGCAACAA CAATTGGTAA AACTCACTGT GATCAATATT TTTATATCAT
     TAAGTAAAAA TATCGTTGTT GTTAACCATT TTGAGTGACA CTAGTTATAA AAATATAGTA 1981 GCAAAATATG TTTAAAATAA AATGAAAATT GTATTAAAAA AAAAAAAAA A
     CGTTTTATAC AAATTTTATT TTACTTTTAA CATAATTTTT TTTTTTTTT T
```

FIG. 1D

| | | |
|---|---|---|
| VRP | -20 | MHLLGFFSVACSLLAAALLPGPREAPAAAAFESGLDLSDAEPDAGEATA |
| VRP | 31 | YASKDLEEQLRSVSSVDELMTVLYPEYWKMYKCQLRKGGWQHNREQANLN |
| VEGF121 | -26 | . . . . . . . . . . . . . . . . . . . . . . . . . . . . . MNFLLSWVHWSLALLLYLHHA |
| PlGF131 | -18 | . . . . . . . . . . . . . . . . . . . . . . . . . . . . . . MPVMRLFPCFLQLLAGLALPA |
| VRP | 81 | SRTEETIKFAAAHYNTEILKSIDNEWRKTQCMPREVCIDVGKEFGVATNT |
| VEGF121 | -5 | KWSQAAPMAEGGGQNHEVVKFMDVYQRSYCHPIETLVDIFQEYPDEIEY |
| PlGF131 | 4 | VPPQQWALSAGNGSSEVEVVPFQEVWGRSYCRALERLVDVSEYPSEVEH |
| VRP | 131 | FFKPPCVSVYRCGGCCNSEGLQCMNTSTSYLSKTLFEITVPLSQGPKPVT |
| VEGF121 | 46 | IFKPSCVPLMRCGGCCNDEGLECVPTEESNITMQIMRIKP. . HQQHIGE |
| PlGF131 | 54 | MFSPSCVSLLRCTGCCGDENLHCVPVETANVTMQLLKIRS. . GDRPSYVE |
| VRP | 181 | ISFANHTSCRCMSKLDVYRQVHSIIRRSLPATLPQCQAANKTCPTNYMWN |
| VEGF121 | 94 | MSFLQHNKCECRPKKDRARQEKCDKPRR |
| PlGF131 | 102 | LTFSQHVRCECRPLREKMKPERCGDAVPRR |
| VRP | 231 | NHICRCLAQEDFMFSSDAGDDSTDGFHDICGPNKELDEETCQCVCRAGLR |
| VRP | 281 | PASCGPHKELDRNSCQCVCKNKLFPSQCGANREFDENTCQCVCKRTCPRN |
| VRP | 331 | QPLNPGKCACECTESPQKCLLKGKKFHHQTCSCYRRPCTNRQKACEPGFS |
| VRP | 381 | YSEEVCRCVPSYWKRPQMS |

FIG. 3B

SEQUENCE LISTING

```
<160> NUMBER OF SEQ ID NOS: 12

<210> SEQ ID NO 1
<211> LENGTH: 2031
<212> TYPE: DNA
<213> ORGANISM: Human
<220> FEATURE:
<221> NAME/KEY: Human
<222> LOCATION: 1-2031
<223> OTHER INFORMATION: Sequence source:  VRP

<400> SEQUENCE: 1
cgcggggtgt tctggtgtcc cccgccccgc ctctccaaaa agctacaccg         50
acgcggaccg cggcggcgtc ctccctcgcc ctcgcttcac ctcgcgggct        100
ccgaatgcgg ggagctcgga tgtccggttt cctgtgaggc ttttacctga        150
cacccgccgc ctttccccgg cactggctgg gagggcgccc tgcaaagttg        200
ggaacgcgga gccccggacc cgctcccgcc gcctccggct cgcccagggg        250
gggtcgccgg gaggagcccg ggggagaggg accaggaggg gcccgcggcc        300
tcgcaggggc gcccgcgccc ccaccccctgc ccccgccagc ggaccggtcc        350 cccaccccg gtccttccac catgcacttg ctgggcttct tctctgtggc        400
gtgttctctg ctcgccgctg cgctgctccc gggtcctcgc gaggcgcccg        450
ccgccgccgc cgccttcgag tccggactcg acctctcgga cgcggagccc        500
gacgcgggcg aggccacggc ttatgcaagc aaagatctgg aggagcagtt        550
acggtctgtg tccagtgtag atgaactcat gactgtactc taccagaat         600 attggaaaat gtacaagtgt cagctaagga aaggaggctg gcaacataac        650
```

-continued

| | |
|---|---|
| agagaacagg ccaacctcaa ctcaaggaca gaagagacta taaaatttgc | 700 |
| tgcagcacat tataatacag agatcttgaa aagtattgat aatgagtgga | 750 |
| gaaagactca atgcatgcca cgggaggtgt gtatagatgt ggggaaggag | 800 |
| tttggagtcg cgacaaacac cttctttaaa cctccatgtg tgtccgtcta | 850 |
| cagatgtggg ggttgctgca atagtgaggg gctgcagtgc atgaacacca | 900 |
| gcacgagcta cctcagcaag acgttatttg aaattacagt gcctctctct | 950 |
| caaggcccca aaccagtaac aatcagtttt gccaatcaca cttcctgccg | 1000 |
| atgcatgtct aaactggatg tttacagaca agttcattcc attattagac | 1050 |
| gttccctgcc agcaacacta ccacagtgtc aggcagcgaa caagacctgc | 1100 |
| cccaccaatt acatgtggaa taatcacatc tgcagatgcc tggctcagga | 1150 |
| agattttatg ttttcctcgg atgctggaga tgactcaaca gatggattcc | 1200 |
| atgacatctg tggaccaaac aaggagctgg atgaagagac tgtcagtgt | 1250 |
| gtctgcagag cggggcttcg gcctgccagc tgtggacccc acaaagaact | 1300 |
| agacagaaac tcatgccagt gtgtctgtaa aaacaaactc ttccccagcc | 1350 |
| aatgtggggc caaccgagaa tttgatgaaa acacatgcca gtgtgtatgt | 1400 |
| aaaagaacct gccccagaaa tcaacccta atcctggaa aatgtgcctg | 1450 |
| tgaatgtaca gaaagtccac agaaatgctt gttaaaagga agaagttcc | 1500 |
| accaccaaac atgcagctgt tacagacggc catgtacgaa ccgccagaag | 1550 |
| gcttgtgagc caggattttc atatagtgaa gaagtgtgtc gttgtgtccc | 1600 |
| ttcatattgg aaaagaccac aaatgagcta agattgtact gttttccagt | 1650 |
| tcatcgattt tctattatgg aaaactgtgt tgccacagta gaactgtctg | 1700 |
| tgaacagaga gacccttgtg ggtccatgct aacaaagaca aaagtctgtc | 1750 |
| tttcctgaac catgtggata actttacaga aatggactgg agctcatctg | 1800 |
| caaaaggcct cttgtaaaga ctggttttct gccaatgacc aaacagccaa | 1850 |
| gatttttcctc ttgtgatttc tttaaaagaa tgactatata atttatttcc | 1900 |
| actaaaaata ttgttctgc attcatttttt atagcaacaa caattggtaa | 1950 |
| aactcactgt gatcaatatt tttatatcat gcaaatatg tttaaaataa | 2000 |
| aatgaaaatt gtattaaaaa aaaaaaaaaa a | 2031 |

<210> SEQ ID NO 2
<211> LENGTH: 2031
<212> TYPE: DNA
<213> ORGANISM: Human
<220> FEATURE:
<221> NAME/KEY: Human
<222> LOCATION: 1-2031
<223> OTHER INFORMATION: Sequence source: complement to SEQ ID NO. 1

<400> SEQUENCE: 2

| | |
|---|---|
| tttttttttt ttttttaata caatttcat tttattttaa acatattttg | 50 |
| catgatataa aaatattgat cacagtgagt tttaccaatt gttgttgcta | 100 |
| taaaaatgaa tgcagaaaca atatttttag tggaaataaa ttatatagtc | 150 |
| attcttttaa agaaatcaca agaggaaaat cttggctgtt tggtcattgg | 200 |
| cagaaaacca gtcttacaa gaggcctttt gcagatgagc tccagtccat | 250 |
| ttctgtaaag ttatccacat ggttcaggaa agacagactt ttgtctttgt | 300 |

| | |
|---|---|
| tagcatggac ccacaagggt ctctctgttc acagacagtt ctactgtggc | 350 |
| aacacagttt tccataatag aaaatcgatg aactggaaaa cagtacaatc | 400 |
| ttagctcatt tgtggtcttt tccaatatga agggacacaa cgacacactt | 450 |
| cttcactata tgaaaatcct ggctcacaag ccttctggcg gttcgtacat | 500 |
| ggccgtctgt aacagctgca tgtttggtgg tggaacttct ttccttttaa | 550 |
| caagcatttc tgtggacttt ctgtacattc acaggcacat tttccaggat | 600 |
| ttaggggttg atttctgggg caggttcttt tacatacaca ctggcatgtg | 650 |
| ttttcatcaa attctcggtt ggccccacat tggctgggga agagtttgtt | 700 |
| tttacagaca cactggcatg agtttctgtc tagttctttg tggggtccac | 750 |
| agctggcagg ccgaagcccc gctctgcaga cacactgaca ggtctcttca | 800 |
| tccagctcct tgtttggtcc acagatgtca tggaatccat ctgttgagtc | 850 |
| atctccagca tccgaggaaa acataaaatc ttcctgagcc aggcatctgc | 900 |
| agatgtgatt attccacatg taattggtgg ggcaggtctt gttcgctgcc | 950 |
| tgacactgtg gtagtgttgc tggcagggaa cgtctaataa tggaatgaac | 1000 |
| ttgtctgtaa acatccagtt tagacatgca tcggcaggaa gtgtgattgg | 1050 |
| caaaactgat tgttactggt ttggggcctt gagagagagg cactgtaatt | 1100 |
| tcaaataacg tcttgctgag gtagctcgtg ctggtgttca tgcactgcag | 1150 |
| cccctcacta ttgcagcaac ccccacatct gtagacggac acacatggag | 1200 |
| gtttaaagaa ggtgtttgtc gcgactccaa actccttccc cacatctata | 1250 |
| cacacctccc gtggcatgca ttgagtcttt ctccactcat tatcaatact | 1300 |
| tttcaagatc tctgtattat aatgtgctgc agcaaatttt atagtctctt | 1350 |
| ctgtccttga gttgaggttg gcctgttctc tgttatgttg ccagcctcct | 1400 |
| ttccttagct gacacttgta cattttccaa tattctgggt agagtacagt | 1450 |
| catgagttca tctacactgg acacagaccg taactgctcc tccagatctt | 1500 |
| tgcttgcata agccgtggcc tcgcccgcgt cgggctccgc gtccgagagg | 1550 |
| tcgagtccgg actcgaaggc ggcggcgcg cggggcgcct cgcgaggacc | 1600 |
| cgggagcagc acagcggcga gcagagaaca cgccacagag aagaagccca | 1650 |
| gcaagtgcat ggtggaagga ccgggggtgg gggaccggtc cgctggcggg | 1700 |
| ggcagggtg ggggcgcggg cgcccctgcg aggccgcggg cccctcctgg | 1750 |
| tccctctccc ccgggctcct cccggcgacc cccctgggc gagccggagg | 1800 |
| cggcgggagc gggtccgggg ctccgcgttc ccaactttgc agggcgccct | 1850 |
| cccagccagt accggggaaa ggcggcgggt gtcaggtaaa agcctcacag | 1900 |
| gaaaccggac atccgagctc cccgcattcg gagcccgcga ggtgaagcga | 1950 |
| gggcgaggga ggacgccgcc gcggtccgcg tcggtgtagc tttttggaga | 2000 |
| ggcggggcgg gggacaccag aacaccccgc g | 2031 |

```
<210> SEQ ID NO 3
<211> LENGTH: 419
<212> TYPE: PRT
<213> ORGANISM: Human
<220> FEATURE:
<221> NAME/KEY: Human
<222> LOCATION: 1-419
```

<223> OTHER INFORMATION: Sequence source: VRP

<400> SEQUENCE: 3

```
Met His Leu Leu Gly Phe Phe Ser Val Ala Cys Ser Leu Leu Ala
 1               5                  10                  15

Ala Ala Leu Leu Pro Gly Pro Arg Glu Ala Pro Ala Ala Ala Ala
                20                  25                  30

Ala Phe Glu Ser Gly Leu Asp Leu Ser Asp Ala Glu Pro Asp Ala
                35                  40                  45

Gly Glu Ala Thr Ala Tyr Ala Ser Lys Asp Leu Glu Glu Gln Leu
                50                  55                  60

Arg Ser Val Ser Ser Val Asp Glu Leu Met Thr Val Leu Tyr Pro
                65                  70                  75

Glu Tyr Trp Lys Met Tyr Lys Cys Gln Leu Arg Lys Gly Gly Trp
                80                  85                  90

Gln His Asn Arg Glu Gln Ala Asn Leu Asn Ser Arg Thr Glu Glu
                95                 100                 105

Thr Ile Lys Phe Ala Ala Ala His Thr Asn Thr Glu Ile Leu Lys
               110                 115                 120

Ser Ile Asp Asn Glu Trp Arg Lys Thr Gln Cys Met Pro Arg Glu
               125                 130                 135

Val Cys Ile Asp Val Gly Lys Glu Phe Gly Val Ala Thr Asn Thr
               140                 145                 150

Phe Phe Lys Pro Pro Cys Val Ser Val Tyr Arg Cys Gly Gly Cys
               155                 160                 165

Cys Asn Ser Glu Gly Leu Gln Cys Met Asn Thr Ser Thr Ser Tyr
               170                 175                 180

Leu Ser Lys Thr Leu Phe Glu Ile Thr Val Pro Leu Ser Gln Gly
               185                 190                 195

Pro Lys Pro Val Thr Ile Ser Phe Ala Asn His Thr Ser Cys Arg
               200                 205                 210

Cys Met Ser Lys Leu Asp Val Tyr Arg Gln Val His Ser Ile Ile
               215                 220                 225

Arg Arg Ser Leu Pro Ala Thr Leu Pro Gln Cys Gln Ala Ala Asn
               230                 235                 240

Lys Thr Cys Pro Thr Asn Tyr Met Trp Asn Asn His Ile Cys Arg
               245                 250                 255

Cys Leu Ala Gln Glu Asp Phe Met Phe Ser Ser Asp Ala Gly Asp
               260                 265                 270

Asp Ser Thr Asp Gly Phe His Asp Ile Cys Gly Pro Asn Lys Glu
               275                 280                 285

Leu Asp Glu Glu Thr Cys Gln Cys Val Cys Arg Ala Gly Leu Arg
               290                 295                 300

Pro Ala Ser Cys Gly Pro His Lys Glu Leu Asp Arg Asn Ser Cys
               305                 310                 315

Gln Cys Val Cys Lys Asn Lys Leu Phe Pro Ser Gln Cys Gly Ala
               320                 325                 330

Asn Arg Glu Phe Asp Glu Asn Thr Cys Gln Cys Val Cys Lys Arg
               335                 340                 345

Thr Cys Pro Arg Asn Gln Pro Leu Asn Pro Gly Lys Cys Ala Cys
               350                 355                 360

Glu Cys Thr Glu Ser Pro Gln Lys Cys Leu Leu Lys Gly Lys Lys
               365                 370                 375
```

```
Phe His His Gln Thr Cys Ser Cys Tyr Arg Arg Pro Cys Thr Asn
              380                 385                 390

Arg Gln Lys Ala Cys Glu Pro Gly Phe Ser Tyr Ser Glu Glu Val
              395                 400                 405

Cys Arg Cys Val Pro Ser Tyr Trp Lys Arg Pro Gln Met Ser
              410                 415             419

<210> SEQ ID NO 4
<211> LENGTH: 147
<212> TYPE: PRT
<213> ORGANISM: Human
<220> FEATURE:
<221> NAME/KEY: Human
<222> LOCATION: 1-147
<223> OTHER INFORMATION: Sequence source: VEGE-121

<400> SEQUENCE: 4

Met Asn Phe Leu Leu Ser Trp Val His Trp Ser Leu Ala Leu Leu
  1               5                  10                  15

Leu Tyr Leu His His Ala Lys Trp Ser Gln Ala Ala Pro Met Ala
                 20                  25                  30

Glu Gly Gly Gly Gln Asn His His Glu Val Val Lys Phe Met Asp
                 35                  40                  45

Val Tyr Gln Arg Ser Tyr Cys His Pro Ile Glu Thr Leu Val Asp
                 50                  55                  60

Ile Phe Gln Glu Tyr Pro Asp Glu Ile Glu Tyr Ile Phe Lys Pro
                 65                  70                  75

Ser Cys Val Pro Leu Met Arg Cys Gly Gly Cys Cys Asn Asp Glu
                 80                  85                  90

Gly Leu Glu Cys Val Pro Thr Glu Glu Ser Asn Ile Thr Met Gln
                 95                 100                 105

Ile Met Arg Ile Lys Pro His Gln Gly Gln His Ile Gly Glu Met
                110                 115                 120

Ser Phe Leu Gln His Asn Lys Cys Glu Cys Arg Pro Lys Lys Asp
                125                 130                 135

Arg Ala Arg Gln Glu Lys Cys Asp Lys Pro Arg Arg
                140                 145     147

<210> SEQ ID NO 5
<211> LENGTH: 149
<212> TYPE: PRT
<213> ORGANISM: Human
<220> FEATURE:
<221> NAME/KEY: Human
<222> LOCATION: 1-149
<223> OTHER INFORMATION: Sequence source: PIGE-131

<400> SEQUENCE: 5

Met Pro Val Met Arg Leu Phe Pro Cys Phe Leu Gln Leu Leu Ala
  1               5                  10                  15

Gly Leu Ala Leu Pro Ala Val Pro Pro Gln Gln Trp Ala Leu Ser
                 20                  25                  30

Ala Gly Asn Gly Ser Ser Glu Val Glu Val Val Pro Phe Gln Glu
                 35                  40                  45

Val Trp Gly Arg Ser Tyr Cys Arg Ala Leu Glu Arg Leu Val Asp
                 50                  55                  60

Val Val Ser Glu Tyr Pro Ser Glu Val Glu His Met Phe Ser Pro
                 65                  70                  75

Ser Cys Val Ser Leu Leu Arg Cys Thr Gly Cys Cys Gly Asp Glu
```

```
                    80                 85                 90
Asn Leu His Cys Val Pro Val Glu Thr Ala Asn Val Thr Met Gln
                95                100                105
Leu Leu Lys Ile Arg Ser Gly Asp Arg Pro Ser Tyr Val Glu Leu
               110                115                120
Thr Phe Ser Gln His Val Arg Cys Glu Cys Arg Pro Leu Arg Glu
               125                130                135
Lys Met Lys Pro Glu Arg Cys Gly Asp Ala Val Pro Arg Arg
               140                145                149

<210> SEQ ID NO 6
<211> LENGTH: 299
<212> TYPE: DNA
<213> ORGANISM: Unknown
<220> FEATURE:
<223> OTHER INFORMATION: Sequence source:  EST
<220> FEATURE:
<221> NAME/KEY: unsure
<222> LOCATION: 74
<223> OTHER INFORMATION: unknown base

<400> SEQUENCE: 6
ccgtctacag atgtgggggt tgctgcaata gtgaggggct gcagtgcatg              50
aacaccagca cgagctacct cagnaagacg ttatttgaaa ttacagtgcc             100
tctctctcaa ggccccaaac cagtaacaat cagttttgcc aatcacactt             150
cctgccgatg catgtctaaa ctggatgttt acagacaagt tcattccatt             200
attagacgtt ccctgccagc aacactacca cagtgtcagg cagcgaacaa             250
gacctgcccc accaattaca tgtggaataa tcacatctgc agatgcctg              299

<210> SEQ ID NO 7
<211> LENGTH: 50
<212> TYPE: DNA
<213> ORGANISM: Artificial sequence
<220> FEATURE:
<223> OTHER INFORMATION: Sequence source:  synthetic probe

<400> SEQUENCE: 7
ctggtgttca tgcactgcag cccctcacta ttgcagcaac ccccacatct              50

<210> SEQ ID NO 8
<211> LENGTH: 50
<212> TYPE: DNA
<213> ORGANISM: Artificial sequence
<220> FEATURE:
<223> OTHER INFORMATION: Sequence source:  synthetic probe

<400> SEQUENCE: 8
gcatctgcag atgtgattat tccacatgta attggtgggg caggtcttgt              50

<210> SEQ ID NO 9
<211> LENGTH: 8
<212> TYPE: PRT
<213> ORGANISM: Human
<220> FEATURE:
<221> NAME/KEY: Human
<222> LOCATION: 1-8
<223> OTHER INFORMATION: Sequence source:  Flt4 partial sequence

<400> SEQUENCE: 9

Tyr Ser Met Thr Pro Pro Thr Leu
 1               5           8
```

```
<210> SEQ ID NO 10
<211> LENGTH: 9
<212> TYPE: PRT
<213> ORGANISM: Human
<220> FEATURE:
<221> NAME/KEY: Human
<222> LOCATION: 1-9
<223> OTHER INFORMATION: Sequence source:  Flt4 partial sequence

<400> SEQUENCE: 10

Ser Leu Arg Arg Arg Gln Gln Gln Asp
 1               5               9

<210> SEQ ID NO 11
<211> LENGTH: 40
<212> TYPE: PRT
<213> ORGANISM: Unknown
<220> FEATURE:
<223> OTHER INFORMATION: Sequence source:  Herpes glycoprotein D partial
      sequence

<400> SEQUENCE: 11

Lys Tyr Ala Leu Ala Asp Ala Ser Leu Lys Met Ala Asp Pro Asn
 1               5                  10                  15

Arg Phe Arg Gly Lys Asp Leu Pro Val Leu Asp Gln Leu Leu Glu
                20                  25                  30

Gly Gly Ala Ala His Tyr Ala Leu Leu Pro
                35                  40

<210> SEQ ID NO 12
<211> LENGTH: 13
<212> TYPE: PRT
<213> ORGANISM: Human
<220> FEATURE:
<221> NAME/KEY: Human
<222> LOCATION: 1-13
<223> OTHER INFORMATION: Sequence source:  partial VRP sequence

<400> SEQUENCE: 12

Gly Pro Arg Glu Ala Pro Ala Ala Ala Ala Ala Phe Glu
 1               5                  10          13
```

VEGF-RELATED PROTEIN

PRIORITY OF INVENTION

This application is a divisional of pending U.S. patent application Ser. No. 10/346,802, filed on Jan. 17, 2003, now abandoned, which is a divisional of 09/313,299, filed on May 17, 1999, now U.S. Pat. No. 6,576,608, which is a divisional application of U.S. patent application Ser. No. 08/706,054, filed on Aug. 30, 1996, now U.S. Pat. No. 6,451,764, which claims the benefit of U.S. Provisional Application Ser. No. 60/003,491, filed on Sep. 8, 1995. All of these applications are hereby expressly incorporated by reference.

BACKGROUND OF THE INVENTION

1. Field of the Invention

The present invention pertains generally to a receptor protein tyrosine kinase (rPTK) ligand. More particularly, the invention relates to a novel ligand, designated VEGF-related protein (VRP) or VH1, which binds to, and stimulates the phosphorylation of, the Flt4 tyrosine kinase receptor (also known as the Sal-S1 receptor) and the isolation and recombinant production of the same.

2. Description of Related Art

The formation of new blood vessels either from differentiating endothelial cells during embryonic development (vasculogenesis) or from pre-existing vessels during adult life (angiogenesis) is an essential feature of organ development, reproduction, and wound healing in higher organisms. Folkman and Shing, *J. Biol. Chem.*, 267: 10931-10934 (1992); Reynolds et al., *FASEB J.*, 6: 886-892 (1992); Risau et al., *Development*, 102: 471-478 (1988). Angiogenesis is also necessary for certain pathological processes including tumorigenesis (Folkman, *Nature Medicine*, 1: 27-31 [1995]) and retinopathy. Miller et al., *Am. J. Pathol.*, 145: 574-584 (1994). While several growth factors can stimulate angiogenesis (Klagsbrun and D'Amore, *Ann. Rev. Physiol.*, 53: 217-239 [1991]; Folkman and Klagsbrun, *Science*, 235: 442-447 [1987]), vascular endothelial growth factor (VEGF) (Ferrara et al., *Endo. Rev.*, 13: 18-32 [1992]) is a potent angiogenic factor that acts via the endothelial cell-specific receptor tyrosine kinases fms-like tyrosine kinase (Flt1) (Shibuya et al., *Oncogene*, 5: 519-524 [1990]; deVries et al., *Science*, 255: 989-991 [1992]) and fetal liver kinase (Flk1) (also designated KDR). Quinn et al., *Proc. Natl. Acad. Sci. USA*, 90: 7533-7537 (1993); Millauer et al., *Cell*, 72: 835-846 (1993); Matthews et al., *Proc. Natl. Acad. Sci. USA*, 88: 9026-9030 (1991); Terman et al., *Biochem. Biophys. Res. Commun.*, 187: 1579-1586 (1992); Terman et al., *Oncogene*, 6: 1677-1683 (1991); Oelrichs et al., *Oncogene*, 8: 11-18 (1993). These two VEGF receptors and a third orphan receptor, Flt4 (Pajusola et al., *Cancer Res.*, 52: 5738-5743 [1992]; Galland et al., *Oncogene*, 8: 1233-1240 [1993]; Finnerty et al., *Oncogene*, 8: 2293-2298 [1993]) constitute a subfamily of class III receptor tyrosine kinases that contain seven extracellular immunoglobulin-like domains and a split intracellular tyrosine kinase domain. Mustonen and Alitalo, *J. Cell. Biol.*, 129: 895-898 (1995). See also WO 94/10202 published 11 May 1994 and PCT/US93/00586 filed 22 Jan. 1993 (Avraham et al.). These three receptors have 31-36% amino acid identity in their extracellular ligand-binding domains.

Mice deficient in Flt1 (Fong et al., *Nature*, 376: 66-70 [1995]) or Flk1 (Shalaby et al., *Nature*, 376: 62-66 [1995]) (generated by gene targeting in embryonic stem cells) have severe defects in vasculogenesis and die in utero at embryonic day 8-9. The phenotype of the receptor-deficient mice differs considerably, however. Mice lacking Flt1 have a disorganized vascular endothelium that extends to the major vessels as well as to the microvasculature, while endothelial cell differentiation appears to be normal. Fong et al., supra. Mice lacking Flk1 have a major defect in the development of mature endothelial cells as well as a severe reduction in hematopoietic cell progenitors. Shalaby et al., supra. Thus, VEGF may act on endothelial cells at more than one stage of vasculogenesis.

Flt4 is also specifically expressed in endothelial cells; it is first observed in day 8.5 mouse embryos in endothelial cell precursors. Kaipainen et al., *Proc. Natl. Acad. Sci. USA*, 92: 3566-3570 (1995); Kaipainen et al., *J. Exp. Med.*, 178: 2077-2088 (1993). See also Hatva et al., *Am J. Pathol.*, 146: 368-378 (1995). As development proceeds, Flt4 expression becomes confined to the venous and lymphatic endothelium and is finally restricted to the lymphatic vessels. Consistent with this finding, adult human tissues show Flt4 expression in lymphatic endothelia while there is a lack of expression in arteries, veins, and capillaries. Kaipainen et al., *Proc. Natl. Acad. Sci. USA*, supra. Clones encoding human and mouse Flt4 have been isolated either by PCR with primers from conserved tyrosine kinase regions (Finnerty et al., supra; PCT/US93/00586, supra; Aprelikova et al., *Cancer Res.*, 52: 746-748 [1992]) or by low-stringency hybridization with a Flk2 probe. Galland et al., *Genomics*, 13: 475-478 (1992). Alternative splicing of the Flt4 mRNA produces two variants of the protein differing by 65 amino acids at the C-terminus. Pajusola et al., *Oncogene*, 8: 2931-2937 (1993). These variants migrate as bands of 170-190 kDa that are partially cleaved proteolytically in the extracellular domain to produce a form of about 125 kDa. Pajusola et al., *Oncogene*, 8, supra; Pajusola et al., *Oncogene*, 9: 3545-3555 (1994). Expression of the longer spliced form of Flt4 as a chimera with the extracellular domain of the CSF-1 receptor shows that the Flt4 intracellular domain can signal a ligand-dependent growth response in rodent fibroblasts. Pajusola et al., *Oncogene*, 9, supra; Borg et al., *Oncogene*, 10: 973-984 (1995). Flt4 has been localized to human chromosome 5q34-q35 (Aprelikova et al., supra; Galland et al., *Genomics*, supra); Flt1 and Flk1 are located at 13q12 (Imbert et al., *Cytogenet. Cell Genet.*, 67: 175-177 [1994]) and 4q12. Sait et al., *Cytogenet. Cell Genet.*, 70: 145-146 (1995); Spritz et al., *Genomics*, 22: 431-436 (1994).

VEGF is a homodimeric, cysteine-rich protein that can occur in at least four forms due to alternative splicing of its mRNA. Ferrara et al., supra. While VEGF is a high-affinity ligand for Flt1 and Flk1, it does not bind or activate Flt4. Pajusola et al., *Oncogene*, 9, supra. The only other closely related member of the VEGF family is placental growth factor (PlGF), which has 47% amino acid identity with VEGF. Maglione et al., *Proc. Natl. Acad. Sci. USA*, 88: 9267-9271 (1991). PlGF also occurs in two alternatively spliced forms which differ in the presence or absence of a basic heparin binding domain of 21 amino acids. Maglione et al., *Oncogene*, 8: 925-931 (1993); Hauser and Weich, *Growth Factors*, 9: 259-268 (1993). PlGF binds to Flt1 but not to Flk1 (Park et al., *J. Biol. Chem.*, 269: 25646-25654 [1994]); it is believed that its binding to Flt4 has not been determined. PlGF fails to duplicate the capillary endothelial cell mitogenesis or vascular permeability activities of VEGF, suggesting that these activities are mediated by the Flk1 receptor. Park et al., supra.

Molecules that modulate the Flk1 receptor or neutralize activation of a VEGF receptor are disclosed in the patent literature. For example, WO 95/21613 published 17 Aug. 1995 discloses compounds that modulate KDR/Flk1 receptor signal transduction so as to regulate and/or modulate vasculogenesis and angiogenesis and disclose using Flk1 to evaluate and screen for drugs and analogs of VEGF involved in Flk1 modulation by either agonist or antagonist activities; WO 95/21865 published 17 Aug. 1995 discloses molecules immunointeractive with animal neuroepithelial kinase (NYK)/Flk1, which molecules can be used to provide agents for treatment, prophylaxis, and diagnosis of an angiogenic-dependent phenotype; and WO 95/21868 published 17 Aug. 1995 discloses monoclonal antibodies that specifically bind to an extracellular domain of a VEGF receptor and neutralize activation of the receptor.

SUMMARY OF THE INVENTION cDNA clones have now been identified that encode a novel protein, designated VRP, which binds to and stimulates the phosphorylation of the receptor tyrosine kinase Flt4. VRP is related in amino acid sequence to VEGF, but does not interact appreciably with the VEGF receptors, Flt1 and Flk1.

In one aspect, the invention provides isolated biologically active human VRP containing at least 265 amino acids. In another aspect, the invention supplies isolated biologically active human VEGF-related protein (VRP) comprising an amino acid sequence comprising at least residues +1 through 29, inclusive, of FIG. 1. In further aspect, the invention supplies isolated biologically active human VRP comprising an amino acid sequence shown as residues −20 through 399, inclusive, or residues 1 through 399, inclusive, of FIG. 1.

The invention also pertains to chimeras comprising the VRP fused to another polypeptide. For example, the invention provides a chimeric polypeptide comprising the VRP fused to a tag polypeptide sequence. An example of such a chimera is epitope-tagged VRP.

In another aspect, the invention provides a composition comprising biologically active VRP and a pharmaceutically acceptable carrier. In a more specific embodiment, the invention provides a pharmaceutical composition useful for promotion of vascular or lymph endothelial cell growth comprising a therapeutically effective amount of the VRP in a pharmaceutically acceptable carrier. In another aspect, this composition further comprises another cell growth factor such as VEGF and/or PDGF.

In a further aspect, the invention provides a method of treating vascular tissue and promoting angiogenesis in a mammal comprising administering to the mammal an effective amount of the composition comprising VRP. In another embodiment, the invention provides a method for treating trauma affecting the vascular endothelium comprising administering to a mammal suffering from said trauma an effective amount of the composition containing the VRP. The trauma is, for example, diabetic ulcers or a wound of the blood vessels or heart. In another embodiment, the invention provides a method for treating a dysfunctional state characterized by lack of activation or lack of inhibition of a receptor for VRP in a mammal comprising administering to the mammal an effective amount of the composition containing the VRP.

The invention also provides a method which involves contacting the Flt4 receptor with the VRP to cause phosphorylation of the kinase domain thereof. For example, the invention provides a method for stimulating the phosphorylation of a tyrosine kinase domain of a Flt4 receptor comprising contacting an extracellular domain of the Flt4 receptor with the VRP.

The invention also provides a monoclonal antibody which binds to the VRP and preferably also neutralizes a biological activity of the protein, one biological activity being characterized as promoting neovascularization or vascular permeability or vascular endothelial cell growth in a mammal.

Alternatively or conjunctively, the invention provides a monoclonal antibody which binds to the N-terminal portion from residues −20 through 137, inclusive, or from residues +1 through 137, inclusive, of the amino acid sequence shown in FIG. 1. The antibody can be used, for example, to detect the presence of the VRP in a biological sample suspected of having the protein, or to treat patients. The invention contemplates a pharmaceutical composition comprising such antibody and a pharmaceutically acceptable carrier, as well as a method of treating diseases or disorders characterized by undesirable excessive neovascularization or vascular permeability in a mammal comprising administering to said mammal an effective amount of one of the antibodies described above. Further included by the invention is a method for treating a dysfunctional state characterized by excessive activation or inhibition of a receptor for VRP in a mammal comprising administering to the mammal an effective amount of one of the antibodies described above.

In addition, the invention contemplates a peptide consisting of an amino acid sequence shown as residues −20 through −1, inclusive, of FIG. 1.

In a further embodiment, the invention provides an isolated nucleic acid molecule encoding VRP or a VRP chimera. In one aspect, the nucleic acid molecule is RNA or DNA that encodes a biologically active VRP or is complementary to nucleic acid sequence encoding such VRP, and remains stably bound to it under stringent conditions. The nucleic acid molecule optionally includes the regions of the nucleic acid sequences of FIG. 1 which encode signal sequences. In one embodiment, the nucleic acid sequence is selected from:

(a) the coding region of the nucleic acid sequence of FIG. 1 that codes for the preprotein from residue −20 to residue 399 or that codes for the mature protein from residue 1 to residue 399 (i.e., nucleotides 372 through 1628, inclusive, or nucleotides 432 through 1628, inclusive, of the nucleic acid sequence shown in FIG. 1 as SEQ ID NO: 1); or (b) a sequence corresponding to the sequence of (a) within the scope of degeneracy of the genetic code. In another aspect, the nucleic acid molecule can be provided in a replicable vector comprising the nucleic acid molecule operably linked to control sequences recognized by a host cell transfected or transformed with the vector. The invention further provides a host cell comprising the vector or the nucleic acid molecule. A method of producing VRP is also provided which comprises culturing a host cell comprising the nucleic acid molecule and recovering the protein from the host cell culture.

BRIEF DESCRIPTION OF THE DRAWINGS

FIGS. 1A-1D depict the nucleotide coding sequence (SEQ ID NO: 1), nucleotide complementary sequence (SEQ ID NO: 2), and deduced amino acid sequence (SEQ ID NO: 3) of the human VRP described herein.

FIGS. 3A and 3B respectively depict a map of cDNA clones encoding human VRP and an alignment of the protein sequence VRP (SEQ ID NO: 3) with that of $VEGF_{121}$ (SEQ ID NO: 4) and $PlGF_{131}$ (SEQ ID NO: 5). FIG. 3A shows the extent of four VRP cDNA clones; dashed lines indicate the missing portions of VH1.1 and VH1.3. Arrows indicate restriction enzyme sites; the shaded box indicates the putative secretion signal sequence; the open box indicates the mature protein; Y-type designations within the open box indicate the potential N-linked glycosylation sites; and vertical lines indicate the cysteine residues. A diagram of $VEGF_{121}$ is shown for comparison. The hydropathy plot (Kyle and Doolittle, *J. Mol. Biol.*, 157: 105-132 [1982]) is for VRP. In FIG. 3B, overlining indicates the region encoded by an expressed sequence tag (EST) (sequence of a portion of a cDNA clone) from GenBank designated HSC1WF111.

DETAILED DESCRIPTION OF THE PREFERRED EMBODIMENTS

I. Definitions

Figure 2:
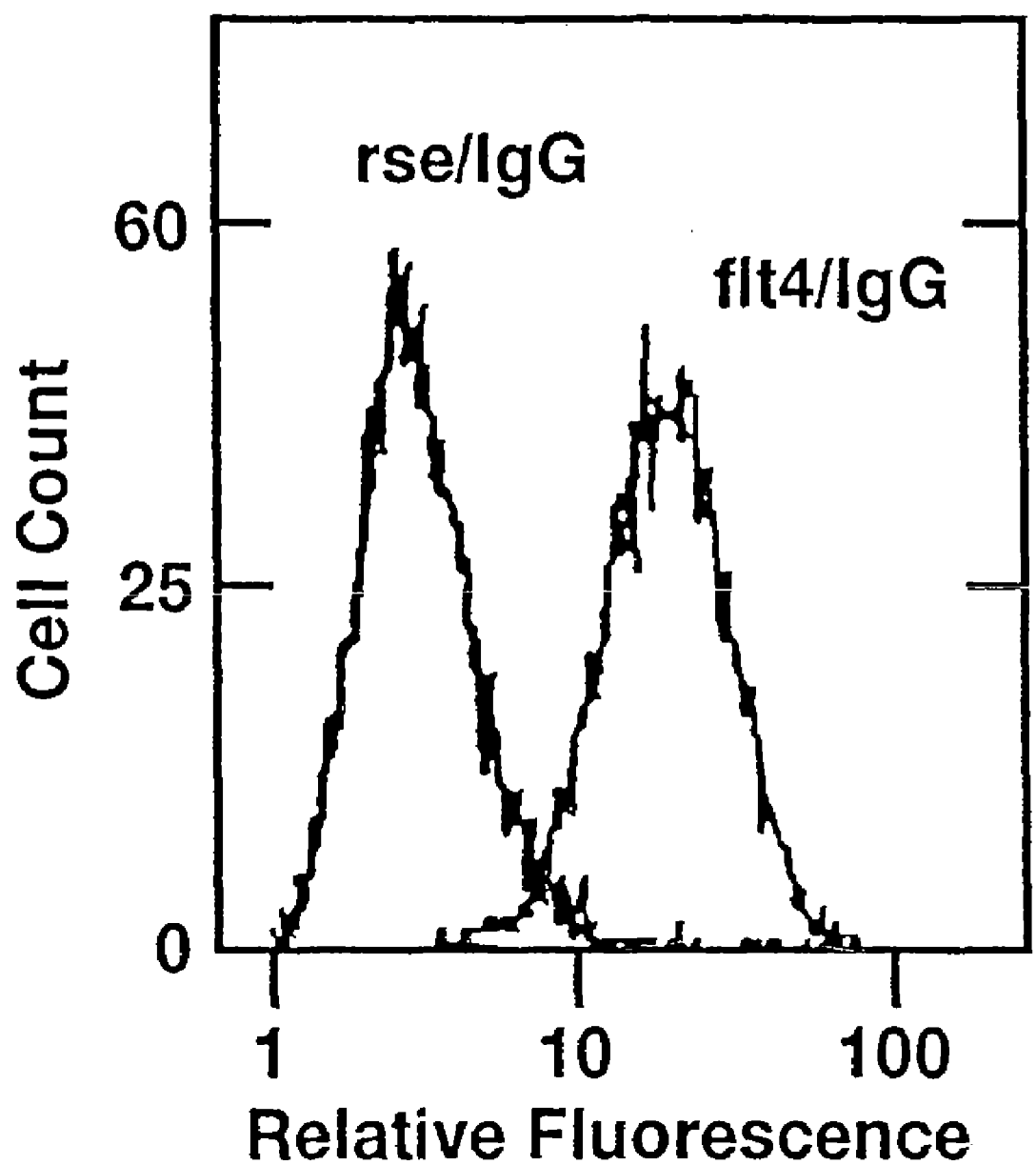
FIG. 2 depicts binding of Flt4/IgG and of Rse/IgG (an unrelated receptor fusion protein) to the human glioma cell line G61, which binding was evaluated by FACS analysis.

In describing the present invention, the following terms will be employed, and are intended to be defined as indicated below.

"Human VRP" is defined herein to be a polypeptide sequence containing at least residues −20 to 399, inclusive, or residues +1 to 399, inclusive, of the amino acid sequence shown in FIG. 1, including residues −5 to 399, inclusive, and residues −4 to 399, inclusive, of the amino acid sequence shown in FIG. 1, as well as biologically active deletional, insertional, or substitutional variants of the above sequences having at least 265 amino acids and/or having at least residues +1 through 29, inclusive, of FIG. 1. In a preferred embodiment, the protein sequence has at least residues +1 through 137, inclusive, of FIG. 1, more preferably at least residues −20 through 29, inclusive, of FIG. 1, and most preferably at least residues −20 through 137, inclusive, of FIG. 1. In another preferred embodiment, the biologically active variants have a length of 265 to about 450 amino acid residues, more preferably about 300-450, even more preferably about 350-450, and most preferably about 399-419 amino acid residues. Another preferred set of variants are variants that are insertional or substitutional variants, or deletional variants where the deletion is in the signal sequence and/or is not in the N-terminal region of the molecule (i.e., residues 1-29, preferably residues 1-137). The definition of VRP excludes all known EST sequences, such as, e.g., H07991, H05134, H05177, HSC1WF112, HSC1WF111, T81481, R77495, H07899, T84377, T81690, and T89295, as well as all forms of VEGF and PlGF.

"Biologically active" for the purposes herein means having the ability to bind to, and stimulate the phosphorylation of, the Flt4 receptor. Generally, the protein will bind to the extracellular domain of the Flt4 receptor and thereby activate or inhibit the intracellular tyrosine kinase domain thereof. Consequently, binding of the protein to the receptor may result in enhancement or inhibition of proliferation and/or differentiation and/or activation of cells having the Flt4 receptor for the VRP in vivo or in vitro. Binding of the protein to the Flt4 receptor can be determined using conventional techniques, including competitive binding methods, such as RIAs, ELISAs, and other competitive binding assays. Ligand/receptor complexes can be identified using such separation methods as filtration, centrifugation, flow cytometry (see, e.g., Lyman et al., *Cell*, 75:1157-1167 [1993]; Urdal et al., *J. Biol. Chem.*, 263:2870-2877 [1988]; and Gearing et al., *EMBO J.*, 8:3667-3676 [1989]), and the like. Results from binding studies can be analyzed using any conventional graphical representation of the binding data, such as Scatchard analysis (Scatchard, *Ann. NY Acad. Sci.*, 51:660-672 [1949]; Goodwin et al., *Cell*, 73:447-456 [1993]), and the like. Since the VRP induces phosphorylation of the Flt4 receptor, conventional tyrosine phosphorylation assays, such as the assay described in Example 5 herein, can also be used as an indication of the formation of a Flt4 receptor/VRP complex.

The term "epitope tagged" when used herein refers to a chimeric polypeptide comprising the entire VRP, or a portion thereof, fused to a "tag polypeptide". The tag polypeptide has enough residues to provide an epitope against which an antibody thereagainst can be made, yet is short enough such that it does not interfere with activity of the VRP. The tag polypeptide preferably also is fairly unique so that the antibody thereagainst does not substantially cross-react with other epitopes. Suitable tag polypeptides generally have at least six amino acid residues and usually between about 8-50 amino acid residues (preferably between about 9-30 residues).

"Isolated," when used to describe the various proteins disclosed herein, means protein that has been identified and separated and/or recovered from a component of its natural environment. Contaminant components of its natural environment are materials that would interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the VRP natural environment will not be present. Ordinarily, however, isolated protein will be prepared by at least one purification step.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

An "isolated" VRP nucleic acid molecule is a nucleic acid molecule that is identified and separated from at least one contaminant nucleic acid molecule with which it is ordinarily associated in the natural source of the VRP nucleic acid. An isolated VRP nucleic acid molecule is other than in the form or setting in which it is found in nature. Isolated VRP nucleic acid molecules therefore are distinguished from the VRP nucleic acid molecule as it exists in natural cells. However, an isolated VRP nucleic acid molecule includes VRP nucleic acid molecules contained in cells that ordinarily express VRP where, for example, the nucleic acid molecule is in a chromosomal location different from that of natural cells.

The isolated VRP polypeptide, VRP nucleic acid, or VRP antibody may be labeled for diagnostic and probe purposes, using a label as described and defined further below in the discussion on uses of VRP antibodies.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-VRP monoclonal antibodies (including agonist and antagonist antibodies) and anti-VRP antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-VRP antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage and Lamoyi, in *Monoclonal Antibody Production Techniques and Applications*, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods. U.S. Pat. No. 4,816,567. The "monoclonal antibodies" may also be isolated from phage libraries generated using the techniques described in McCafferty et al., *Nature*, 348:552-554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

As used herein, "vascular endothelial cell growth factor," or "VEGF," refers to a mammalian growth factor derived originally from bovine pituitary follicular cells having the amino acid sequence of FIG. 2 of WO 90/13649, and has the human amino acid sequence of FIG. 10 of WO 90/13649. See also U.S. Pat. No. 5,194,596, which discloses bovine VEGF of 120 amino acids and human VEGF of 121 amino acids. The biological activity of native VEGF is capable of promoting selective growth of vascular endothelial cells but not of bovine corneal endothelial cells, lens epithelial cells, adrenal cortex cells, BHK-21 fibroblasts, or keratinocytes.

The expression "trauma affecting the vascular endothelium" refers to trauma, such as injuries, to the blood vessels or heart, including the vascular network of organs, to which an animal or human, preferably a mammal, and most preferably a human, is subjected. Examples of such trauma include wounds, incisions, and ulcers, most preferably diabetic ulcers and wounds or lacerations of the blood vessels or heart. Trauma includes conditions caused by internal events as well as those that are imposed by an extrinsic agent such as a pathogen, which can be improved by promotion of vascular endothelial cell growth. It also refers to the treatment of wounds in which neovascularization or re-endothelialization is required for healing.

"Promotion of vascular or lymph endothelial cell growth" refers to inducing or increasing the growth of vascular or lymph endothelial cells, including human lung microvascular endothelial cells.

"Disorders related to vasculogenesis and angiogenesis" include cancer, diabetes, hemangioma, and Kaposi's sarcoma.

"Diseases or disorders characterized by undesirable excessive neovascularization or vascular permeability" refer to diseases or disorders that include, by way of example, excessive neovascularization, tumors, and especially solid malignant tumors, rheumatoid arthritis, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation. Examples of diseases or disorders characterized by undesirable excessive vascular permeability include edema associated with brain tumors, ascites associated with malignancies, Meigs' syndrome, lung inflammation, nephrotic syndrome, pericardial effusion (such as that associated with pericarditis), and pleural effusion.

"Dysfunctional states characterized by excessive activation or inhibition of a receptor for VRP" (such receptor including Flt4) refer to disorders or diseases that would be beneficially treated by providing to a mammal having such a pathological condition an antagonist to VRP, such as a chimera of Flt4 or its extracellular domain (e.g., an IgG fusion with Flt4) or an antibody to VRP.

"Dysfunctional states characterized by lack of activation or lack of inhibition of a receptor for VRP" (such receptor including Flt4) refer to disorders or diseases that would be beneficially treated by providing VRP or a VRP receptor agonist to a mammal with such a pathological condition.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

"Effective amount" or "therapeutically effective amount" of the VRP, VRP composition, antibody, or antibody composition is an amount that is effective either to prevent, lessen the worsening of, alleviate, or cure the treated condition. For example, an effective amount of VRP includes that amount which is sufficient to enhance the growth of vascular endothelium in vivo or to treat trauma, and an "effective amount" of VRP antibody includes that amount which is sufficient to reduce excess neovascularization and angiogenesis.

II. Modes for Carrying Out the Invention

The present invention is based on the discovery of a novel VRP which binds to, and stimulates the phosphorylation of, the Flt4 receptor.

Three approaches were undertaken to identify protein that would bind and stimulate the phosphorylation of the Flt4 receptor. First, the full-length receptor was stably expressed in 293 cells to establish a receptor tyrosine kinase phosphorylation assay of Flt4 activation. This assay was used to screen about 400 cell supernatants and tissue extracts, without positive results.

Second, the extracellular domain of the receptor was expressed as a fusion protein with an immunoglobulin Fc domain. By using this fusion protein (Flt4/IgG) to screen cell lines for membrane-bound ligands by FACS analysis, one positive cell line was identified. The human glioma line, G61, gave about a 10-fold shift in peak fluorescence intensity that was specific for Flt4/IgG (FIG. 2). Attempts to expression clone this putative membrane-bound ligand by the transfection of pools of cDNA clones into COS cells followed by screening with labeled Flt4/IgG gave no positives from 640 pools of 1000-5000 clones each. Flt4/IgG was also used to generate polyclonal antisera and monoclonal antibodies that had agonistic activity and that were used to develop the Flt4 tyrosine phosphorylation assay as described in Example 5 below.

Third, candidate ligand proteins were tested for their ability to bind to Flt4/IgG or to activate the Flt4 phosphorylation assay. Labeled VEGF failed to bind to Flt4/IgG, although the expected binding of VEGF to Flt1/IgG or Flk1/IgG was routinely detected. The failure of VEGF to bind or stimulate the phosphorylation of Flt4 has been reported by Pajusola et al., *Oncogene*, 9, supra. An additional candidate ligand protein was found by use of cloning techniques, details of which are provided in Example 3 below. The human VRP cDNA sequence is depicted in FIG. 1A-1D. The predicted molecular weight of the protein is 44.8 kDa.

A description follows as to how the biologically active human VRP may be prepared.

1. Preparation of VRP

Most of the discussion below pertains to production of VRP by culturing cells transformed with a vector containing VRP nucleic acid and recovering the polypeptide from the cell culture. It is further envisioned that the VRP of this invention may be produced by homologous recombination, as provided for in WO 91/06667, published 16 May 1991.

Briefly, this method involves transforming primary human cells containing a human VRP-encoding gene with a construct (i.e., vector) comprising an amplifiable gene [such as dihydrofolate reductase (DHFR) or others discussed below] and at least one flanking region of a length of at least about 150 bp that is homologous with a DNA sequence at the locus of the coding region of the VRP gene to provide amplification of the VRP gene. The amplifiable gene must be at a site that does not interfere with expression of the VRP gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing VRP are grown so as to express the gene and produce the protein.

A. Isolation of DNA Encoding VRP

The DNA encoding VRP may be obtained from any cDNA library prepared from tissue believed to possess the VRP mRNA and to express it at a detectable level. Accordingly, human VRP DNA can be conveniently obtained from a cDNA library prepared from human brain tissue, e.g., a glial cell line. The VRP-encoding gene may also be obtained from a genomic library or by oligonucleotide synthesis.

Libraries are screened with probes (such as antibodies to the VRP or oligonucleotides of about 20-80 bases) designed to identify the gene of interest or the protein encoded by it. Screening the cDNA or genomic library with the selected probe may be conducted using standard procedures as described in chapters 10-12 of Sambrook et al., *Molecular Cloning: A Laboratory Manual* (New York: Cold Spring Harbor Laboratory Press, 1989). An alternative means to isolate the gene encoding VRP is to use PCR methodology as described in section 14 of Sambrook et al., supra.

A preferred method of practicing this invention is to use carefully selected oligonucleotide sequences to screen cDNA libraries from various human tissues, preferably brain cell lines. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

In some preferred embodiments, the nucleic acid sequence includes the native VRP signal sequence. Nucleic acid having all the protein coding sequence is obtained by screening selected cDNA or genomic libraries using the deduced amino acid sequence disclosed herein for the first time, and, if necessary, using conventional primer extension procedures as described in section 7.79 of Sambrook et al., supra, to detect precursors and processing intermediates of mRNA that may not have been reverse-transcribed into cDNA.

Amino acid sequence variants of VRP are prepared by introducing appropriate nucleotide changes into the VRP DNA, or by synthesis of the desired VRP polypeptide. Such variants represent insertions, substitutions, and/or deletions of, residues within or at one or both of the ends of the amino acid sequence shown for the VRP in FIG. 1. Preferably, these variants represent insertions and/or substitutions within or at one or both ends of the mature sequence, and/or insertions, substitutions and/or deletions within or at one or both of the ends of the signal sequence for VRP shown in FIG. 1. Any combination of insertion, substitution, and/or deletion is made to arrive at the final construct, provided that the final construct possesses the desired biological activity as defined herein. The amino acid changes also may alter post-translational processes of the VRP, such as changing the number or position of glycosylation sites, altering the membrane anchoring characteristics, and/or altering the intracellular location of the VRP by inserting, deleting, or otherwise affecting the leader sequence of the VRP.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. See also, for example, Table I therein and the discussion surrounding this table for guidance on selecting amino acids to change, add, or delete.

B. Insertion of Nucleic Acid into Replicable Vector

The nucleic acid (e.g., cDNA or genomic DNA) encoding native or variant VRP is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The VRPs of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the VRP DNA that is inserted into the vector. The heterologous signal sequence selected preferably is one that is recognized and processed (i.e., cleaved by a signal peptidase) by the host cell. For prokaryotic host cells that do not recognize and process the native VRP signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, alpha factor leader (including *Saccharomyces* and *Kluyveromyces* α-factor leaders, the latter described in U.S. Pat. No. 5,010,182 issued 23 Apr. 1991), or acid phosphatase leader, the *C. albicans* glucoamylase leader (EP 362,179 published 4 Apr. 1990), or the signal described in WO 90/13646 published 15 Nov. 1990. In mammalian cell expression the native signal sequence (e.g., the VRP presequence that normally directs secretion of VRP from human cells in vivo) is satisfactory, although other mammalian signal sequences may be suitable, such as signal sequences from other animal VRPs, and signal sequences from secreted polypeptides of the same or related species, as well as viral secretory leaders, for example, the herpes simplex gD signal.

The DNA for such precursor region is ligated in reading frame to DNA encoding the mature VRP.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of VRP DNA. However, the recovery of genomic DNA encoding VRP is more complex than that of an exogenously replicated vector because restriction enzyme digestion is required to excise the VRP DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.*, 1:327 [1982]), mycophenolic acid (Mulligan et al., *Science*, 209:1422 [1980]) or hygromycin. Sugden et al., *Mol. Cell. Biol.*, 5:410-413 (1985). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the VRP nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes VRP. Amplification is the process by which genes in greater demand for the production of a protein critical for growth are reiterated in tandem within the chromosomes of successive generations of recombinant cells. Increased quantities of VRP are synthesized from the amplified DNA. Other examples of amplifiable genes include met-allothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding VRP. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells [particularly wild-type hosts that contain endogenous DHFR] transformed or co-transformed with DNA sequences encoding VRP, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7. Stinchcomb et al., *Nature*, 282:39 (1979); Kingsman et al., *Gene* 7:141 (1979); Tschemper et al., *Gene* 10:157 (1980). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Bianchi et al., *Curr. Genet.*, 12:185 (1987). More recently, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the VRP nucleic acid. Promoters are untranslated sequences located upstream (5') to the start codon of a structural gene (generally within about 100 to 1000 bp) that control the transcription and translation of particular nucleic acid sequence, such as the VRP nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to VRP-encoding DNA by removing the promoter from the source DNA by restriction enzyme digestion and inserting the isolated promoter sequence into the vector. Both the native VRP promoter sequence and many heterologous promoters may be used to direct amplification and/or expression of the VRP DNA. However, heterologous promoters are preferred, as they generally permit greater transcription and higher yields of VRP as compared to the native VRP promoter.

Promoters suitable for use with prokaryotic hosts include the β-lactamase and lactose promoter systems (Chang et al., *Nature*, 275:615 [1978]; Goeddel et al., *Nature*, 281:544 [1979]), alkaline phosphatase, a tryptophan (trp) promoter system (Goeddel, *Nucleic Acids Res.*, 8:4057 [1980]; EP 36,776), and hybrid promoters such as the tac promoter. deBoer et al., *Proc. Natl. Acad. Sci. USA*, 80:21-25 (1983). However, other known bacterial promoters are suitable. Their nucleotide sequences have been published, thereby enabling a skilled worker operably to ligate them to DNA encoding VRP (Siebenlist et al, *Cell* 20:269 [1980]) using linkers or adaptors to supply any required restriction sites. Promoters for use in bacterial systems also will contain a Shine-Dalgarno (S.D.) sequence operably linked to the DNA encoding VRP.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; Holland, *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

VRP transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the VRP sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422-1427 (1980); Pavlakis et al., *Proc. Natl. Acad. Sci. USA*, 78:7398-7402 (1981). The immediate early promoter of the human cytomegalovirus is conveniently obtained as a HindIII E restriction fragment. Greenaway et al., *Gene*, 18:355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503-508 (1982) on expressing cDNA encoding immune interferon in monkey cells; Reyes et al., *Nature*, 297:598-601 (1982) on expression of human β-interferon cDNA in mouse cells under the control of a thymidine kinase promoter from herpes simplex virus; Canaani and Berg, *Proc. Natl. Acad. Sci. USA* 79:5166-5170 (1982) on expression of the human interferon β1 gene in cultured mouse and rabbit cells; and Gorman et al., *Proc. Natl. Acad. Sci. USA*, 79:6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the VRP of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78:993 [1981]) and 3' (Lusky et al., *Mol. Cell Bio.*, 3:1108 [1983]) to the transcription unit, within an intron (Banerji et al., *Cell*, 33:729 [1983]), as well as within the coding sequence itself. Osborne et al., *Mol. Cell Bio.*, 4:1293 (1984). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature*, 297:17-18 (1982) on enhancing elements for activation of eukaryotic promoters. The enhancer may be spliced into the vector at a position 5' or 3' to the VRP-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding VRP.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

(viii) Transient Expression Vectors

Particularly useful in the practice of this invention are expression vectors that provide for the transient expression in mammalian cells of DNA encoding VRP. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of VRP that are biologically active VRP.

(ix) Suitable Exemplary Vertebrate Cell Vectors

Other methods, vectors, and host cells suitable for adaptation to the synthesis of VRP in recombinant vertebrate cell culture are described in Gething et al., *Nature*, 293:620-625 (1981); Mantei et al., *Nature*, 281:40-46 (1979); EP 117,060; and EP 117,058. A particularly useful plasmid for mammalian cell culture expression of VRP is pRK5 (EP 307,247) or pSVI6B. WO 91/08291 published 13 Jun. 1991.

C. Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonA$\Delta$ ptr3 phoA$\Delta$E15 $\Delta$(argF-lac)169 ompT$\Delta$ degP41kan$^r$. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed. Alternatively still, methods of cloning, e.g., PCR or other nucleic acid polymerase reactions, are suitable.

In addition to prokaryotes, eukaryotic microbes such as filamentous fungi or yeast are suitable cloning or expression hosts for VRP-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature*, 290:140 [1981]; EP 139,383 published 2 May 1985); *Kluyveromyces* hosts (U.S. Pat. No. 4,943,529; Fleer et al., supra) such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus; yarrowia* [EP 402,226]; *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81:1470-1474 [1984]) and *A. niger*. Kelly and Hynes, *EMBO J.*, 4:475-479 (1985).

Suitable host cells for the expression of glycosylated VRP are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6:47-55 (1988); Miller et al., in *Genetic Engineering*, Setlow et al., eds., Vol. 8 (Plenum Publishing, 1986), pp. 277-279; and Maeda et al., *Nature*, 315:592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the VRP-encoding DNA. During incubation of the plant cell culture with *A. tumefaciens*, the DNA encoding the VRP is transferred to the plant cell host such that it is transfected, and will, under appropriate conditions, express the VRP-encoding DNA. In addition, regulatory and signal sequences compatible with plant cells are available, such as the nopaline synthase promoter and polyadenylation signal sequences. Depicker et al., *J. Mol. Appl. Gen.*, 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure. See, e.g., *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 [1977]); baby hamster kidney cells (BHK, ATCC CCL 10); Chinese hamster ovary cells/-DHFR (CHO, Urlaub and Chasin, *Proc. Natl. Acad. Sci. USA*, 77:4216 [1980]); mouse sertoli cells (TM4, Mather, *Biol. Reprod.*, 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 [1982]); MRC 5 cells; FS4 cells; and a human hepatoma line (Hep G2).

Host cells are transfected and preferably transformed with the above-described expression or cloning vectors for VRP production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology*, 52:456-457 (1978) is preferred. General aspects of mammalian cell host system transformations have been described in U.S. Pat. No. 4,399,216 issued 16 Aug. 1983. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology*, 185:527-537 (1990) and Mansour et al., *Nature*, 336:348-352 (1988).

D. Culturing the Host Cells

Prokaryotic cells used to produce the VRP polypeptide of this invention are cultured in suitable media as described generally in Sambrook et al., supra.

The mammalian host cells used to produce the VRP of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58:44 (1979), Barnes and Sato, *Anal. Biochem.*, 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

E. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201-5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734-738 (1980).

Antibodies useful for immunohistochemical staining and/or assay of sample fluids may be either monoclonal or polyclonal, and may be prepared in any mammal. Conveniently, the antibodies may be prepared against a native VRP polypeptide or against a synthetic peptide based on the DNA sequences provided herein as described further in Section 4 below.

F. Purification of VRP Polypeptide

VRP preferably is recovered from the culture medium as a secreted polypeptide, although it also may be recovered from host cell lysates when directly produced without a secretory signal. If the VRP is membrane-bound, it can be released from the membrane using a suitable detergent solution (e.g. Triton-X 100)

When VRP is produced in a recombinant cell other than one of human origin, the VRP is completely free of proteins or polypeptides of human origin. However, it is necessary to purify VRP from recombinant cell proteins or polypeptides to obtain preparations that are substantially homogeneous as to VRP. As a first step, the culture medium or lysate is centrifuged to remove particulate cell debris. VRP thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

In the preferred embodiment, the Flt4 receptor-IgG fusion is immobilized on an affinity chromatography column and the VRP can be isolated by affinity purification using this column. Alternatively, the VRP is joined at its N-terminus to a glycoprotein D sequence and is passed through an affinity chromatography column on which is immobilized an anti-gD monoclonal antibody such as 5B6, which is specific for a glycoprotein D sequence.

VRP variants in which residues have been deleted, inserted, or substituted are recovered in the same fashion as native VRP, taking account of any substantial changes in properties occasioned by the variation. For example, preparation of a VRP fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-VRP column can be employed to absorb the VRP variant by binding it to at least one remaining immune epitope.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native VRP may require modification to account for changes in the character of VRP or its variants upon expression in recombinant cell culture.

G. Covalent Modifications of VRP Polypeptides

Covalent modifications of VRP polypeptides are included within the scope of this invention. Both native VRP and amino acid sequence variants of the VRP may be covalently modified. One type of covalent modification of the VRP is introduced into the molecule by reacting targeted amino acid residues of the VRP with an organic derivatizing agent that is capable of reacting with selected side chains or the N— or C-terminal residues of the VRP.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking VRP to a water-insoluble support matrix or surface for use in the method for purifying anti-VRP antibodies, and vice-versa. Commonly used crosslinking agents include, e.g., 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 [1983]), acetylation of the N-terminal amine, and amidation of any C-terminal carboxyl group.

Another type of covalent modification of the VRP polypeptide included within the scope of this invention comprises altering the native glycosylation pattern of the polypeptide. By altering is meant deleting one or more carbohydrate moieties found in native VRP, and/or adding one or more glycosylation sites that are not present in the native VRP.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxylamino acid, most commonly serine or threonine, although 5-hydroxyproline or 5-hydroxylysine may also be used.

Addition of glycosylation sites to the VRP polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native VRP sequence (for O-linked glycosylation sites). For ease, the VRP amino acid sequence is preferably altered through changes at the DNA level, particularly by mutating the DNA encoding the VRP polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the VRP polypeptide is by chemical or enzymatic coupling of glycosides to the polypeptide. These procedures are advantageous in that they do not require production of the polypeptide in a host cell that has glycosylation capabilities for N— or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 (1981).

Removal of carbohydrate moieties present on the VRP polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duskin et al., *J. Biol. Chem.*, 257:3105 (1982). Tunicamycin blocks the formation of protein-N-glycoside linkages.

Another type of covalent modification of VRP comprises linking the VRP polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant VRP, it will be appreciated that some screening of the recovered variant will be needed to select the optimal variant. A change in the immunological character of the VRP molecule, such as affinity for a given antibody, is also able to be measured by a competitive-type immunoassay. The variant is assayed for changes in the suppression or enhancement of its mitogenic activity by comparison to the activity observed for native VRP in the same assay. For example, one can screen for the ability of the variant VRP to stimulate protein kinase activity of the Flt4 receptor as described in Example 5 herein. Other potential modifications of protein or polypeptide properties such as redox or thermal stability, hydrophobicity, susceptibility to proteolytic degradation, or the tendency to aggregate with carriers or into multimers are assayed by methods well known in the art.

H. Epitope-Tagged VRP

This invention encompasses chimeric polypeptides comprising VRP fused to another polypeptide. In one preferred embodiment, the chimeric polypeptide comprises a fusion of the VRP with a tag polypeptide which provides an epitope to which an anti-tag antibody can selectively bind. The epitope tag is generally placed at the amino- or carboxyl-terminus of the VRP. Such epitope-tagged forms of the VRP are desirable, as the presence thereof can be detected using a labeled antibody against the tag polypeptide. Also, provision of the epitope tag enables the VRP to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., *Mol. Cell. Biol.*, 8:2159-2165 [1988]); the c-myc tag and the 8F9, 3C7, 6E10, G4, B7 and 9E10 antibodies thereto (Evan et al., *Molecular and Cellular Biology*, 5:3610-3616 [1985]); and the Herpes Simplex virus glycoprotein D (gD) tag and its antibody. Paborsky et al., *Protein Engineering*, 3(6):547-553 (1990). Other tag polypeptides have been disclosed. Examples include the Flag-peptide (Hopp et al., *BioTechnology*, 6:1204-1210 [1988]); the KT3 epitope peptide (Martin et al., *Science*, 255:192-194 [1992]); an α-tubulin epitope peptide (Skinner et al., *J. Biol. Chem.*, 266:15163-15166 [1991]); and the T7 gene 10 protein peptide tag. Lutz-Freyermuth et al., *Proc. Natl. Acad. Sci. USA*, 87:6393-6397 (1990). Once the tag polypeptide has been selected, an antibody thereto can be generated using the techniques disclosed herein.

The general methods suitable for the construction and production of epitope-tagged VRP are the same as those disclosed hereinabove with regard to (native or variant) VRP. VRP-tag polypeptide fusions are most conveniently constructed by fusing the cDNA sequence encoding the VRP portion in-frame to the tag polypeptide DNA sequence and expressing the resultant DNA fusion construct in appropriate host cells. Ordinarily, when preparing the VRP-tag polypeptide chimeras of the present invention, nucleic acid encoding the VRP will be fused at its 3' end to nucleic acid encoding the N-terminus of the tag polypeptide, however 5' fusions are also possible.

Epitope-tagged VRP can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged VRP can be eluted from the affinity column by varying the buffer pH or ionic strength or adding chaotropic agents, for example.

2. Therapeutic Uses, Compositions, and Administration of VRP

VRP is believed to find therapeutic use for treating mammals via stimulation or inhibition of growth and/or differentiation and/or activation of cells having the Flt4 receptor or one or more other VRP receptors. Exogenous VRP may be administered to a patient in these circumstances. The human VRP is clearly useful insofar as it can be administered to a human having depressed levels of endogenous VRP, preferably in the situation where such depressed levels lead to a pathological disorder, or where there is lack of activation or inhibition of the Flt4 receptor or one or more other VRP receptors.

Various potential therapeutic uses of VRP include those in which VEGF is useful. Examples of these include uses associated with the vascular endothelium, such as the treatment of traumata to the vascular network, in view of the demonstrated rapid promotion by VEGF of the proliferation of vascular endothelial cells that would surround the traumata and in view of the relationship between VEGF and the VRP established herein. Examples of such traumata that could be so treated include, but are not limited to, surgical incisions, particularly those involving the heart, wounds, including lacerations, incisions, and penetrations of blood vessels, and surface ulcers involving the vascular endothelium such as diabetic, haemophiliac, and varicose ulcers. Other physiological conditions that could be improved based on the selective mitogenic character of the VRP are also included herein.

For the traumatic indications referred to above, the VRP molecule will be formulated and dosed in a fashion consistent with good medical practice taking into account the specific disorder to be treated, the condition of the individual patient, the site of delivery of the VRP, the method of administration, and other factors known to practitioners.

Additional indications for the VRP are in the treatment of full-thickness wounds such as dermal ulcers, including the categories of pressure sores, venous ulcers, and diabetic ulcers, as well as of full-thickness burns and injuries where angiogenesis is required to prepare the burn or injured site for a skin graft or flap. In this case the VRP is either applied directly to the site or it is used to soak the skin or flap that is being transplanted prior to grafting. In a similar fashion, the VRP can be used in plastic surgery when reconstruction is required following a burn or other trauma, or for cosmetic purposes.

Angiogenesis is also important in keeping wounds clean and non-infected. The VRP can therefore be used in association with general surgery and following the repair of cuts and lacerations. It is particularly useful in the treatment of abdominal wounds with a high risk of infection. Neovascularization is also key to fracture repair, since blood vessels develop at the site of bone injury. Administration of the VRP to the site of a fracture is therefore another utility.

In cases where the VRP is being used for topical wound healing, as described above, it may be administered by any of the routes described below for the re-endothelialization of vascular tissue, or more preferably by topical means. In these cases, it will be administered as either a solution, spray, gel, cream, ointment, or dry powder directly to the site of injury. Slow-release devices directing the VRP to the injured site will also be used. In topical applications, the VRP will be applied at a concentration ranging from about 50 to 1,000 µg/mL, either in a single application, or in dosing regimens that are daily or every few days for a period of one week to several weeks. Generally, the amount of topical formulation administered is that which is sufficient to apply from about 0.1 to 100 µg/cm$^2$ of the VRP, based on the surface area of the wound.

The VRP can be used as a post-operative wound healing agent in balloon angioplasty, a procedure in which vascular endothelial cells are removed or damaged, together with compression of atherosclerotic plaques. The VRP can be applied to inner vascular surfaces by systemic or local intravenous application either as intravenous bolus injection or infusions. If desired, the VRP can be administered over time using a micrometering pump. Suitable compositions for intravenous administration comprise the VRP in an amount effective to promote endothelial cell growth and a parenteral carrier material. The VRP can be present in the composition over a wide range of concentrations, for example, from about 50 µg/mL to about 1,000 µg/mL using injections of 3 to 10 mL per patient, administered once or in dosing regimens that allow for multiple applications. Any of the known parenteral carrier vehicles can be used, such as normal saline or 5-10% dextrose.

The VRP can also be used to promote endothelialization in vascular graft surgery. In the case of vascular grafts using either transplanted vessels or synthetic material, for example, the VRP can be applied to the surfaces of the graft and/or at the junctions of the graft and the existing vasculature to promote the growth of vascular endothelial cells. For such applications, the VRP can be applied intravenously as described above for balloon angioplasty or it can be applied directly to the surfaces of the graft and/or the existing vasculature either before or during surgery. In such cases it may be desired to apply the VRP in a thickened carrier material so that it will adhere to the affected surface. Suitable carrier materials include, for example, 1-5% carbopol. The VRP can be present in the carrier over a wide range of concentrations, for example, from about 50 µg/mg to about 1,000 µg/mg. Alternatively, the VRP can be delivered to the site by a micrometering pump as a parenteral solution.

The VRP can also be employed to repair vascular damage following myocardial infarction and to circumvent the need for coronary bypass surgery by stimulating the growth of a collateral circulation. The VRP is administered intravenously for this purpose, either in individual injections or by micrometering pump over a period of time as described above or by direct infusion or injection to the site of damaged cardial muscle.

Therapeutic formulations of VRP are prepared for storage by mixing VRP having the desired degree of purity with optional physiologically acceptable carriers, excipients, or stabilizers (*Remington's Pharmaceutical Sciences,* 16th edition, Osol, A., Ed., [1980]), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The VRP also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences,* supra.

VRP to be used for in vivo administration must be sterile. This is readily accomplished by filtration through sterile filtration membranes, prior to or following lyophilization and reconstitution. VRP ordinarily will be stored in lyophilized form or in solution.

Therapeutic VRP compositions generally are placed into a container having a sterile access port, for example, an intravenous solution bag or vial having a stopper pierceable by a hypodermic injection needle.

The route of VRP administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. VRP is administered continuously by infusion or by bolus injection. Generally, where the disorder permits, one should formulate and dose the VRP for site-specific delivery. This is convenient in the case of wounds and ulcers.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethyl-methacrylate) as described by Langer et al., *J. Biomed. Mater. Res.*, 15:167-277 (1981) and Langer, *Chem. Tech.*, 12:98-105 (1982) or poly(vinylalcohol)], polylactides (U.S. Pat. No. 3,773,919, EP 58,481), copolymers of L-glutamnic acid and gamma ethyl-L-glutamate (Sidman et al., *Biopolymers,* 22:547-556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release VRP compositions also include liposomally entrapped VRP. Liposomes containing VRP are prepared by methods known per se: DE 3,218,121; Epstein et al., *Proc. Natl. Acad. Sci. USA* 82:3688-3692 (1985); Hwang et al., *Proc. Natl. Acad. Sci. USA,* 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal VRP therapy.

When applied topically, the VRP is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the VRP formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VRP held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the VRP is present in an amount of about 300-1000 mg per ml of gel.

An effective amount of VRP to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the VRP until a dosage is reached that achieves the desired effect. A typical daily dosage for systemic treatment might range from about 1 μg/kg to up to 10 mg/kg or more, depending on the factors mentioned above. As an alternative general proposition, the VRP is formulated and delivered to the target site or tissue at a dosage capable of establishing in the tissue a VRP level greater than about 0.1 ng/cc up to a maximum dose that is efficacious but not unduly toxic. This intra-tissue concentration should be maintained if possible by continuous infusion, sustained release, topical application, or injection at empirically determined frequencies. The progress of this therapy is easily monitored by conventional assays.

It is within the scope hereof to combine the VRP therapy with other novel or conventional therapies (e.g., growth factors such as VEGF, acidic or basic fibroblast growth factor (aFGF or bFGF, respectively), platelet-derived growth factor (PDGF), insulin-like growth factor (IGF-I or IGF-II), nerve growth factor (NGF), anabolic steroids, EGF or TGF-α) for enhancing the activity of any of the growth factors, including the VRP, in promoting cell proliferation and repair. It is not necessary that such co-treatment drugs be included per se in the compositions of this invention, although this will be convenient where such drugs are proteinaceous. Such admixtures are suitably administered in the same manner and for the same purposes as the VRP used alone. The useful molar ratio of VRP to such secondary growth factors is typically 1:0.1-10, with about equimolar amounts being preferred.

3. Non-Therapeutic, Diagnostic Uses for VRP

The nucleic acid encoding the VRP may be used as a diagnostic for tissue-specific typing. For example, such procedures as in situ hybridization, Northern and Southern blotting, and PCR analysis may be used to determine whether DNA and/or RNA encoding VRP is present in the cell type(s) being evaluated. VRP nucleic acid or polypeptide may also be used as diagnostic markers. For example, the VRP may be labeled, using the techniques described herein, and expression of nucleic acid molecules encoding a Flt4 receptor or another VRP receptor can be quantified, using the labelled VRP.

If the human VRP-encoding nucleic acid is localized to a human chromosome, the nucleic acid for human VRP can be used as a marker for this human chromosome.

VRP nucleic acid is also useful for the preparation of VRP polypeptide by recombinant techniques exemplified herein.

Isolated VRP polypeptide may be used in quantitative diagnostic assays as a standard or control against which samples containing unknown quantities of VRP may be prepared.

VRP preparations are also useful in generating antibodies, as standards in assays for VRP (e.g., by labeling VRP for use as a standard in a radioimmunoassay, radioreceptor assay, or enzyme-linked immunoassay), for detecting the presence of the Flt4 receptor or one or more other VRP receptors in a biological sample (e.g., using a labeled VRP), in affinity purification techniques, and in competitive-type receptor binding assays when labeled with radioiodine, enzymes, fluorophores, spin labels, or the like.

The VRP is also useful as a diagnostic tool. For example, the VRP can be produced in prokaryotic cells using the techniques elaborated herein and the unglycosylated protein so produced can be used as a molecular weight marker. The deduced molecular weight (mw) of the VRP is about 44.8 kDa. To use the VRP as a molecular weight marker, gel filtration chromatography or SDS-PAGE, for example, will be used to separate protein(s) for which it is desired to determine their molecular weight(s) in substantially the normal way. The VRP and other molecular weight markers will be used as standards to provide a range of molecular weights. For example, phosphorylase b (mw=97,400), bovine serum albumin (mw=68,000), ovalbumin (mw=46,000), VRP (mw=44,800), trypsin inhibitor (mw=20,100), and lysozyme (mw=14,400) can be used a mw markers. The other molecular weight markers mentioned here can be purchased commercially from Amersham Corporation, Arlington Heights, Ill., for example. Often, the molecular weight markers will be labeled to enable easy detection following separation. Techniques for labeling antibodies and proteins are discussed herein and are well known in the art. For example, the molecular weight markers may be biotinylated and, following separation on SDS-PAGE, for example, the blot can be incubated with streptavidin-horseradish peroxidase. The bands can then be detected by light detection.

It may also be useful to grow certain cells having the Flt4 receptor or one or more other VRP receptors ex vivo using the VRP as an angiogenic factor or growth factor. Thus, for example, the VRP can be used as a growth factor in the in vitro culturing of endothelial cells. For such uses, the VRP can be added to the cell culture medium at a concentration from about 10 pg/mL to about 10 ng/mL.

These cells which are to be grown ex vivo may simultaneously be exposed to other known growth factors or cytokines. Exemplary cytokines include the interleukins (e.g., IL-3), granulocyte-macrophage colony-stimulating factor (GM-CSF), VEGF, macrophage colony-stimulating factor (M-CSF), granulocyte colony-stimulating factor (G-CSF), granulocyte-macrophage colony-stimulating factor (GM-CSF), erythropoietin (Epo), lymphotoxin, steel factor (SLF), tumor necrosis factor (TNF), and gamma-interferon. This results in proliferation and/or differentiation of the cells having the Flt4 receptor or one or more other VRP receptors.

In yet another aspect of the invention, the VRP may be used for affinity purification of the Flt4 receptor or one or more other VRP receptors. Briefly, this technique involves covalently attaching the VRP to an inert and porous matrix (e.g., agarose reacted with cyanogen bromide). A solution containing the Flt4 receptor or other VRP receptor(s) can then be passed through the chromatographic material and can be subsequently released by changing the elution conditions (e.g. by changing pH or ionic strength).

The purified VRP, and the nucleic acid encoding it, may also be sold as reagents for mechanism studies of VRP and its cognate receptors, to study the role of the VRP and the Flt4 receptor or other VRP receptors in normal growth and development, as well as abnormal growth and development, e.g. in malignancies.

The VRP may be used for competitive screening of potential agonists or antagonists for binding to the Flt4 receptor or other VRP receptors. VRP variants are useful as standards or controls in assays for the VRP, provided that they are recognized by the analytical system employed, e.g. an anti-VRP antibody.

4. VRP Antibody Preparation

A description follows as to the production of exemplary antibodies as defined herein. These exemplary antibodies include polyclonal, monoclonal, humanized, bispecific, or heteroconjugate antibodies.

A. Polyclonal Antibodies

Polyclonal antibodies to the VRP generally are raised in animals by multiple subcutaneous (sc) or intraperitoneal (ip) injections of the VRP and an adjuvant. It may be useful to conjugate the VRP to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg of 1 µg of conjugate (for rabbits or mice, respectively) with 3 volumes of 5 Freud's complete adjuvant and injecting the solution intradermally at multiple sites. One month later the animals are boosted with ⅕ to ⅒ the original amount of conjugate in Freud's complete adjuvant by subcutaneous injection at multiple sites. Seven to 14 days later the animals are bled and the serum is assayed for anti-VRP antibody titer. Animals are boosted until the titer plateaus. Preferably, the animal is boosted with a conjugate of the same VRP with a different protein and/or the conjugation is through a different cross-linking reagent. Conjugates also can be made in recombinant cell culture as protein fusions. Also, aggregating agents such as alum are used to enhance the immune response.

B. Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-VRP monoclonal antibodies of the invention may be made using the hybridoma method first described by Kohler and Milstein, *Nature,* 256:495 (1975), or may be made by recombinant DNA methods. U.S. Pat. No. 4,816,567.

In the hybridoma method, a mouse or other appropriate host animal, such as hamster, is immunized as hereinabove described to elicit lymphocytes that produce, or are capable of producing, antibodies that will specifically bind to the protein used for immunization. Alternatively, lymphocytes may be immunized in vitro. Lymphocytes then are fused with myeloma cells using a suitable fusing agent, such as PEG, to form a hybridoma cell. Goding, *Monoclonal Antibodies: Principles and Practice,* pp. 59-103 (Academic Press, 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif., USA, and SP-2 cells available from the American Type Culture Collection, Rockville, Md. USA. Human myeloma and mouse-human heteromyeloma cell lines also have been described for the production of human monoclonal antibodies. Kozbor, *J. Immunol.,* 133:3001 (1984); Brodeur et al., *Monoclonal Antibody Production Techniques and Applications,* pp. 51-63 (Marcel Dekker, Inc., New York, 1987). See, also, Boerner et al., *J. Immunol.,* 147:86-95 (1991) and WO 91/17769, published 28 Nov. 1991, for techniques for the production of human monoclonal antibodies.

Culture medium in which hybridoma cells are growing is assayed for production of monoclonal antibodies directed against VRP. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, *Anal. Biochem.,* 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice,* pp. 59-104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA,* 90:2551-255 (1993); Jakobovits et al., *Nature,* 362:255-258 (1993).

In a further embodiment, antibodies or antibody fragments can be isolated from antibody phage libraries generated using the techniques described in McCafferty et al., *Nature,* 348: 552-554 (1990), using the VRP to select for a suitable antibody or antibody fragment. Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high-affinity (nM range) human antibodies by chain shuffling (Mark et al., *Bio/Technol.,* 10:779-783 [1992]), as well as combinatorial infection and in vivo recombination as a strategy for constructing very large phage libraries. Waterhouse et al., *Nuc. Acids Res.,* 21:2265-2266 (1993). Thus, these techniques are viable alternatives to traditional monoclonal antibody hybridoma techniques for isolation of "monoclonal" antibodies (especially human antibodies) that are encompassed by the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy- and light-chain constant domains in place of the homologous murine sequences (Morrison et al., *Proc. Nat. Acad. Sci. USA,* 81, 6851 [1984]), or by covalently joining to the immunoglobulin coding sequence all or part of the coding sequence for a non-inmuunoglobulin polypeptide. In that manner, "chimeric" or "hybrid" antibodies are prepared that have the binding specificity of an anti-VRP monoclonal antibody herein.

Typically, such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an VRP and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I; a fluorescent or chemiluminescent compound, such as fluorescein isothiocyanate, rhodamine, or luciferin; or an enzyme, such as alkaline phosphatase, beta-galactosidase, or horseradish peroxidase.

Any method known in the art for separately conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard (which may be a VRP, or an immunologically reactive portion thereof) to compete with the test sample analyte (VRP) for binding with a limited amount of antibody. The amount of VRP in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected (VRP). In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

C. Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 [1986]; Riechmann et al., *Nature* 332:323-327 [1988]; Verhoeyen et al., *Science*, 239:1534-1536 [1988]), by substituting rodent CDRs or CDR sequences for the corresponding sequences of a human antibody. Accordingly, such "humanized" antibodies are chimeric antibodies (U.S. Pat. No. 4,816,567, supra), wherein substantially less than an intact human variable domain has been substituted by the corresponding sequence from a non-human species. In practice, humanized antibodies are typically human antibodies in which some CDR residues, and possibly some FR residues, are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see WO 92/22653, published 23 Dec. 1992.

D. Bispecific Antibodies

Bispecific antibodies are monoclonal, preferably human or humanized, antibodies that have binding specificities for at least two different antigens. In the present case, one of the binding specificities is for the VRP, the other one is for any other antigen, and preferably for a receptor or receptor subunit. For example, bispecific antibodies specifically binding the Flt4 receptor and the VRP are within the scope of the present invention.

Methods for making bispecific antibodies are known in the art. Traditionally, the recombinant production of bispecific antibodies is based on the co-expression of two immunoglobulin heavy-chain/light-chain pairs, where the two heavy chains have different specificities. Millstein and Cuello, *Nature*, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule, which is usually done by affinity chromatography steps, is rather cumbersome, and the product yields are low. Similar procedures are disclosed in WO 93/08829, published 13 May 1993, and in Traunecker et al., *EMBO J.*, 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published 3 Mar. 1994. For further details of generating bispecific antibodies see, for example, Suresh et al., *Methods in Enzymology,* 121:210 (1986).

E. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection. WO 91/00360; WO 92/200373; EP 03089. Heteroconjugate antibodies may be made using any convenient cross-linking methods. Suitable cross-linking agents are well known in the art, and are disclosed, for example, in U.S. Pat. No. 4,676,980, along with a number of cross-linking techniques.

5. Uses of VRP Antibodies i. Therapeutic Uses

VRP antibodies may be useful in certain therapeutic indications to block activity of the VRP (for example, to block excess activation or inhibition of the Flt4 receptor or another receptor that binds to VRP, and to block neovascularization, re-endothelialization, and angiogenesis). Specifically, the VRP antibodies are useful in the treatment of various neoplastic and non-neoplastic diseases and disorders. Neoplasms and related conditions that are amenable to treatment include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Non-neoplastic conditions that are amenable to treatment include rheumatoid arthritis, psoriasis, atherosclerosis, diabetic and other retinopathies, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

Age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VRP antibodies of the present invention are expected to be especially useful in reducing the severity of AMD.

For therapeutic applications, the VRP antibodies of the invention are administered to a mammal, preferably a human, in a pharmaceutically acceptable dosage form, including those that may be administered to a human intravenously as a bolus or by continuous infusion over a period of time, by intramuscular, intraperitoneal, intra-cerobrospinal, subcutaneous, intra-articular, intrasynovial, intrathecal, oral, topical, or inhalation routes. The VRP antibodies also are suitably administered by intratumoral, peritumoral, intralesional, or perilesional routes or to the lymph, to exert local as well as systemic therapeutic effects. The intraperitoneal route is expected to be particularly useful, for example, in the treatment of ovarian tumors.

Such dosage forms encompass pharmaceutically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of VRP antibodies include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The VRP antibody will typically be formulated in such vehicles at a concentration of about 0.1 mg/ml to 100 mg/ml.

Suitable examples of sustained-release preparations include semipermeable matrices of solid hydrophobic polymers containing the VRP antibody, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and gamma ethyl-L-glutamate (Sidman et al., supra), non-degradable ethylene-vinyl acetate (Langer et al., supra), degradable lactic acid-glycolic acid copolymers such as the Lupron Depot™ (injectable micropheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated VRP antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release VRP antibody compositions also include liposomally entrapped antibodies. Liposomes containing the VRP antibodies are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal VRP antibody therapy. Liposomes with enhanced circulation time are disclosed in U.S. Pat. No. 5,013,556.

Another use of the present invention comprises incorporating VRP antibodies into formed articles. Such articles can be used in modulating endothelial cell growth and angiogenesis. In addition, tumor invasion and metastasis may be modulated with these articles.

For the prevention or treatment of disease, the appropriate dosage of VRP antibody will depend on the type of disease to be treated, as defined above, the severity and course of the disease, whether the antibodies are administered for preventive or therapeutic purposes, previous therapy, the patient's clinical history and response to the VRP antibody, and the discretion of the attending physician. The VRP antibody is suitably administered to the patient at one time or over a series of treatments.

Depending on the type and severity of the disease, about 1 µg/kg to 15 mg/kg of VRP antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays, including, for example, radiographic tumor imaging.

According to another embodiment of the invention, the effectiveness of the VRP antibody in preventing or treating disease may be improved by administering the VRP antibody serially or in combination with another proteinaceous agent that is effective for those purposes, such as those enumerated below, or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Also, the VRP antibody is suitably administered serially or in combination with radiological treatments, whether involving irradiation or administration of radioactive substances.

In one embodiment, vascularization of tumors is attacked in combination therapy. One or more VRP antibodies are administered to tumor-bearing patients at therapeutically effective doses as determined, for example, by observing necrosis of the tumor or its metastatic foci, if any. This therapy is continued until such time as no further beneficial effect is observed or clinical examination shows no trace of the tumor or any metastatic foci. Then the proteinaceous auxiliary agent is administered, alone or in combination with another auxiliary agent. Such agents include, e.g., TNF, an antibody capable of inhibiting or neutralizing the angiogenic activity of aFGF or bFGF or hepatocyte growth factor (HGF), an rhVEGF antagonist as described in WO 94/10202, supra, alpha-, beta-, or gamma-interferon, anti-HER2 antibody, heregulin, anti-heregulin antibody, D-factor, interleukin-1 (IL-1), interleukin-2 (IL-2), GM-CSF, or agents that promote microvascular coagulation in tumors, such as anti-protein C antibody, anti-protein S antibody, or C4b binding protein (WO 91/01753 published 21 Feb. 1991), or heat or radiation.

Since the auxiliary agents will vary in their effectiveness it is desirable to compare their impact on the tumor by matrix screening in conventional fashion. The administration of VRP antibody and TNF and/or other auxiliary agent is repeated until the desired clinical effect is achieved. Alternatively, the VRP antibody or antibodies are administered together with TNF and, optionally, other auxiliary agent(s). In instances where solid tumors are found in the limbs or in other locations susceptible to isolation from the general circulation, the therapeutic agents described herein are administered to the isolated tumor or organ. In other embodiments, a FGF or platelet-derived growth factor (PDGF) antagonist, such as an anti-FGF or an anti-PDGF neutralizing antibody, is administered to the patient in conjunction with the VRP antibody. Treatment with VRP antibodies optimally may be suspended during periods of wound healing or desirable neovascularization.

ii. Other Uses

The VRP antibodies of the invention also are useful as affinity purification agents. In this process, the antibodies against VRP are immobilized on a suitable support, such a Sephadex resin or filter paper, using methods well known in the art. The immobilized antibody then is contacted with a sample containing the VRP to be purified, and thereafter the support is washed with a suitable solvent that will remove substantially all the material in the sample except the VRP, which is bound to the immobilized antibody. Finally, the support is washed with another suitable solvent, such as glycine buffer, pH 5.0, that will release the VRP from the antibody.

VRP antibodies may also be useful in diagnostic assays for VRP, e.g., detecting its expression in specific cells, tissues, or serum. The antibodies are labeled in the same fashion as VRP described above and/or are immobilized on an insoluble matrix. VRP antibodies also are useful for the affinity purification of VRP from recombinant cell culture or natural sources. VRP antibodies that do not detectably cross-react with other proteins can be used to purify VRP free from these other known proteins. Suitable diagnostic assays for VRP and its antibodies are described above.

III. Experimental

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLE 1

Isolation of cDNA Clones Encoding Human Flt4 Receptor cDNA synthesized from mRNA purified from the human megakaryocyte leukemia cell line CMK11-5 was amplified with redundant PCR primers based on the conserved regions of tyrosine kinase receptors. Wilks, *Proc. Natl. Acad. Sci. USA*, 86: 1603-1607 (1989). One amplified fragment of about 180 bp with a unique DNA sequence (designated SAL-S1 or tk1; PCT/US93/00586, supra) was used to screen (Janssen et al, supra) cDNA libraries from CMK11-5 and DAMI cells to obtain overlapping clones that encoded the full-length short form of Flt4 receptor (1298 amino acids). The sequence of the assembled Flt4-encoding clones matched that reported from an anerythroleukemia cell line (Pajusola et al., *Cancer Res.*, supra); it encodes 8 amino acid differences from another reported Flt4 sequence. Galland et al., *Oncogene, supra*. Clones encoding the long form of Flt4 (1363 amino acids) were constructed by synthesizing the differing 3' DNA sequence of about 200 bp based on the published sequence. Pajusola et al., *Oncogene*, 8, supra.

EXAMPLE 2

Receptor IgG Fusion Proteins, Flt4/IgG Antiserum, and G61 FACS Analysis

Flt1/IgG (Park et al., supra), Flk1/IgG (Park et al., supra), Rse/IgG (Godowski et al., *Cell*, 82: 355-358 [1995]), and Htk/IgG (Bennett et al., *J. Biol. Chem.*, 269: 14211-14218 [1994]) were produced as described in these references. For Flt4/IgG, DNA encoding the extracellular domain of the Flt4 receptor (amino acids 1-775) was spliced to the Fc region of a human IgG heavy chain at the unique BstEII site in the plasmid pBSSK-Fc (pBSSK-CH2CH3). Bennett et al., *J. Biol. Chem.*, 266: 23060-23067 (1991). The open reading frame encoding Flt4/IgG was cloned in the mammalian expression vector pRK5 (Suva et al., *Science*, 237: 893-896 [1987]) to yield the plasmid pRK5.tk1ig1.1. This plasmid was transfected by electroporation (Janssen et al., supra) into 293 cells (ATCC CRL 1651), and after 3-4 days, Flt4/IgG was purified from the serum-free conditioned medium with protein A agarose (Calbiochem). Flt4 antiserum was generated by injection of purified Flt4/IgG into rabbits.

By using this fusion protein to screen cell lines for membrane-bound VRP by FACS analysis, one positive cell line was identified, G61, described below.

The human glioma cell line, G61 (Hamel et al., *J. Neurosci. Res.*, 34: 147-157 [1993]), was cultured in F12:DMEM (50:50) (high glucose) containing 10% fetal bovine serum, 2 mM L-glutamine, and antibiotics. For FACS analysis of Flt4/IgG binding to G61 cells, 1 million cells were incubated with 70 nM receptor-IgG fusion protein in phosphate-buffered saline (PBS), 5% goat serum, 2% rabbit serum for 60 min. at 4° C. and then stained with 10 μg/mL biotin-SP-conjugated goat anti-human Fc antibody and 10 μg/mL R-phycoerythrin-conjugated streptavidin (Jackson Immuno Research). G61 caused about a 10-fold shift in peak fluorescence intensity that was specific for Flt4/IgG as compared to Rse/IgG, an unrelated tyrosine kinase receptor complex (FIG. 2). Attempts to expression clone this putative membrane-bound VRP by the transfection of pools of cDNA clones into COS cells followed by screening with labeled Flt4/IgG yielded no positives from 640 pools of 1000-5000 clones each.

EXAMPLE 3

Isolation of cDNA Clones Encoding Human VRP

A cDNA library was prepared from polyA+ RNA isolated as described in Cathala et al., *DNA:* 2: 329-335 (1983) and Aviv and Leder, *Proc. Natl. Acad. Sci. USA*, 69: 1408-1412 (1972) from the human glioma cell line, G61. Hamel et al., supra. cDNA was prepared from this RNA with reagents from GIBCO/BRL (SuperScript) and cloned in the plasmid pRK5B (Holmes et al., *Science*, 253: 1278-1280 [1991]) digested with XhoI and NotI. Clones encoding VRP were isolated by screening the cDNA library with synthetic oligo-nucleotide probes based on an EST sequence (GenBank locus HSC1WF111), which showed a reasonable match to VEGF. The EST sequence of HSC1WF111 is 299 bp and is 36% identical to VEGF over 50 residues, including an 11 of 13 residue match beginning at VEGF amino acid 56. The sequence is as follows:

(SEQ ID NO: 6)
5'-CCGTCTACAGATGTGGGGGTTGCTGCAATAGTGAGGGGCTGCAGTGC
ATGAACACCAGCACGAGCTACCTCAGNAAGACGTTATTTGAAATTACAGT
GCCTCTCTCTCAAGGCCCCAAACCAGTAACAATCAGTTTTGCCAATCACA
CTTCCTGCCGATGCATGTCTAAACTGGATGTTTACAGACAAGTTCATTCC
ATTATTAGACGTTCCCTGCCAGCAACACTACCACAGTGTCAGGCAGCGAA
CAAGACCTGCCCCACCCAATTACATGTGGAATAATCACATCTGCAGATGCC
TG.

The sequences of the oligonucleotide probes ovh1.4 and ovh1.5 employed are indicated below.

ovh1.4:
(SEQ ID NO: 7)
5'-CTGGTGTTCATGCACTGCAGCCCCTCACTATTGCAGCAACCCCCACA
TCT ovh1.5:
(SEQ ID NO: 8)
5'-GCATCTGCAGATGTGATTATTCCACATGTAATTGGTGGGCAGGTCT
TGT These two probes were $^{32}$P labeled and hybridized in 20% formamide at 42° C. with a final wash in 30 mM NaCl/3 mM trisodium citrate at 55° C. Janssen, *Current Protocols in Molecular Biology*, John Wiley & Sons (1995). Seven positives were identified and characterized from 650,000 clones screened. The positives fell into three groups by restriction mapping and DNA sequencing.

Clones VH1.4 (pRK.vh1.4.1) and VH1.6 included the full coding region (FIG. 3A) and were sequenced completely. They differ only in length and the lack of two T's preceeding the 3' poly A sequence in VH1.6. Clone VH1.2 is collinear with VH1.4. Clones VH1.3, VH1.5, and VH1.7 are identical and have a 557 bp deletion when compared with VH1.4 (a deletion of bp 519-1075), and clone VH1.1 has a 152 bp deletion when compared with VH1.4 (a deletion of bp 924-1075). The nucleotide and deduced amino acid sequences of VH1.4 are shown in FIG. 1.

The sequence contained an open reading frame of 419 amino acids beginning with an ATG codon preceded by a purine residue at position −3 as expected for a translation initiation site. Kozak, *Nucl. Acids Res.*, 12: 857-872 (1984). About 250 bp 5' of this ATG are two in-frame ATG codons followed shortly (4 or 10 amino acids) by a stop codon. Both of these ATG's have a pyrimidine at position −3 and would not be expected to function as a strong translation initiation site. Kozak, supra. The encoded amino acid sequence imediately following the start of the 419 amino acid reading frame is hydrophobic, indicative of an amino-terminal secretion signal sequence. Perlman and Halvorson, *J. Mol. Biol.*, 167: 391-409 (1983). See FIG. 3A. The most likely cleavage site for this sequence would be after amino acid 20, although cleavage following residues 15 or 16 cannot be excluded. von Heijne, *Nucl. Acids Res.*, 14: 4683-4690 (1986). The open reading frame is preceded by a GC-rich 5' untranslated region of about 380 bp and followed by a 3' untranslated region of about 400 bp.

Figure 3A:
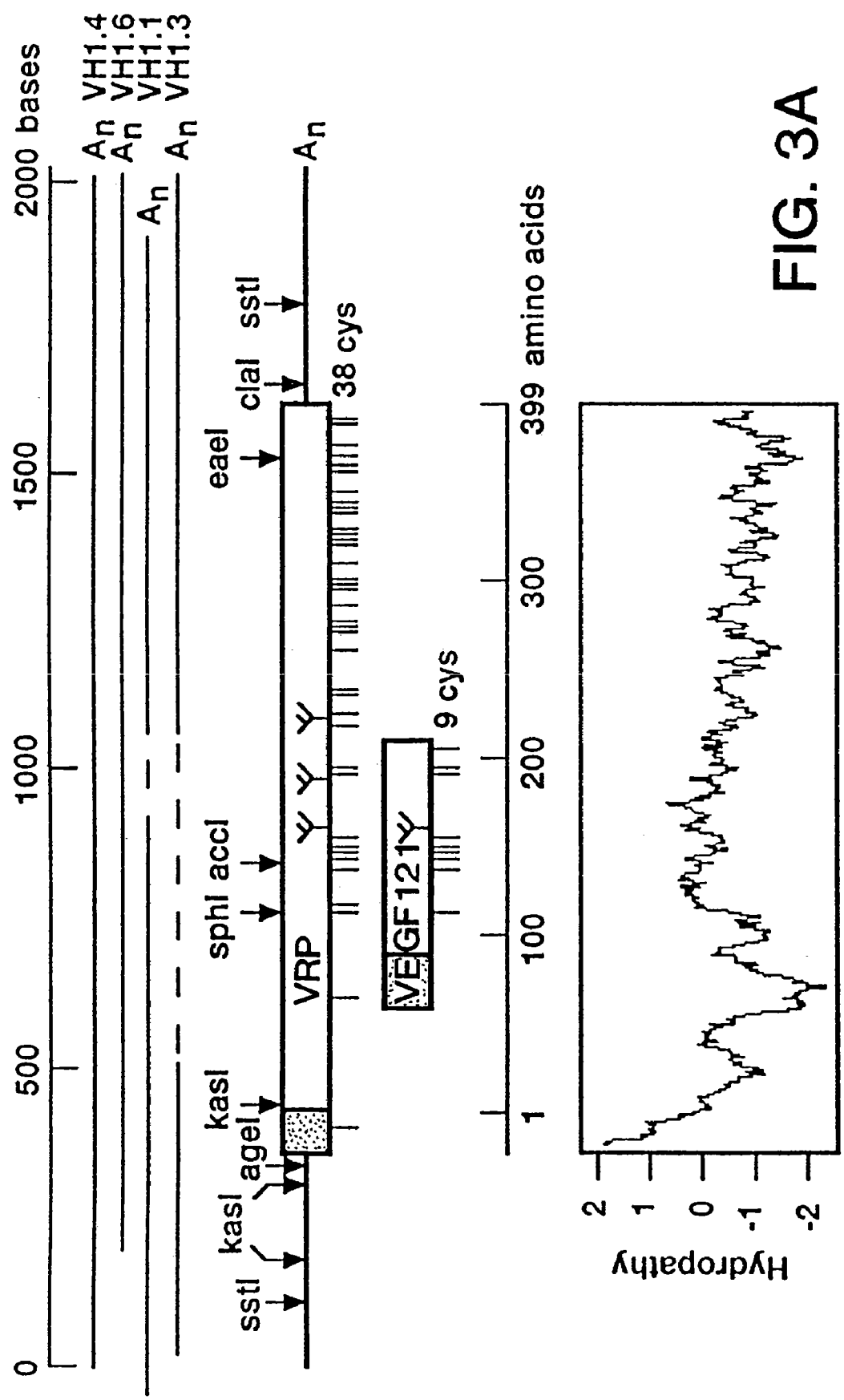

The predicted mature amino acid sequence of human VRP contains 399 amino acid residues (translated $M_r$=44.8 kDa), of which 37 (9.3%) are cysteine residues; there are three potential N-linked glycosylation sites (FIG. 3A). An alignment of the amino acid sequence of VRP with the six forms of VEGF and PlGF shows that it is most similar to $VEGF_{121}$ (32% identical) and $PlGF_{131}$ (27% identical) (FIG. 3B); the locations of 8 of the 9 cysteine residues are conserved. While VRP does not contain the regions of basic amino acids found in some forms of VEGF and PlGF, it is considerably larger than VEGF and contains a cysteine-rich C-terminal half of the molecule that is not found in VEGF. This cysteine-rich domain has four copies of the pattern Cys followed by ten non-Cys residues followed by Cys-X followed by Cys-X and then by Cys (FIG. 3B), a repeat found more than 50 times in a diptran Balbiani ring 3 protein. Paulsson et al., *J. Mol. Biol.*, 211: 331-349 (1990). Without being limited to any one theory, VRP may interact with other membrane-bound proteins on these cells via the cysteine residues; such an intermolecular interaction has been proposed for the Balbiani protein. Paulsson et al., supra.

Two of the cDNA clones (VH1.1 and VH1.3) contained a 152 or 557 bp deletion when compared with VH1.4 (FIG. 3A). Both these deletions end at the same nucleotide and are presumed to be the result of alternative splicing. Both deletions would be expected to encode the same frame-shifted protein 3' of the deletion which terminates at a stop codon within 15 amino acids. The protein encoded by VH1.3 would include none of the core cysteine region similar with VEGF. VH1.1 contains much of the region that is similar to VEGF; its deletion, however, is not analogous to the various known forms of VEGF or PlGF. Ferrara et al., supra; Maglione et al., supra; Hauser and Weich, supra.

Figure 4:
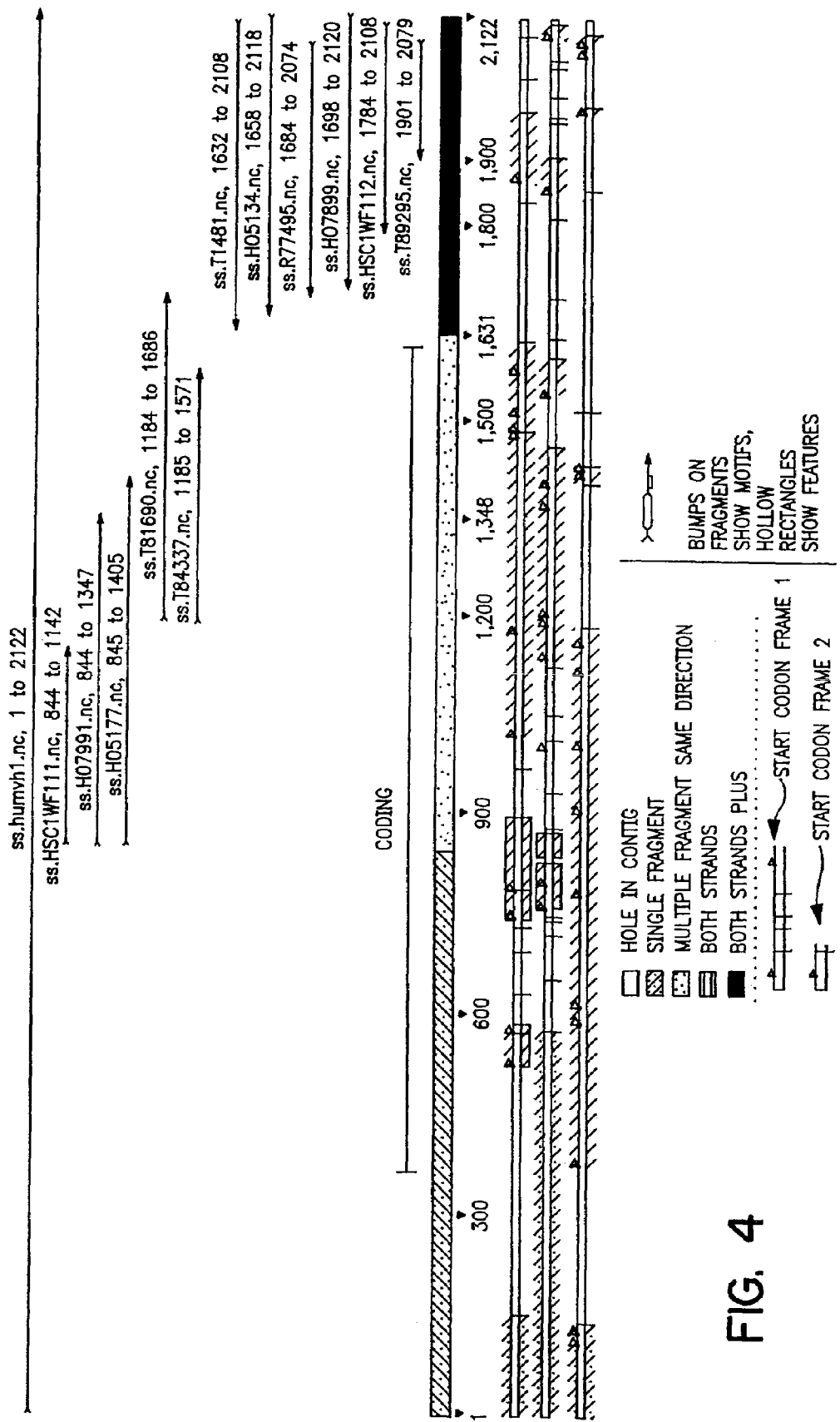
FIG. 4 depicts a map of the cDNA clone for full-length human VRP herein versus eleven known EST's. The eleven EST partial amino acid sequence fragments are H07991 and H07899 (5' and 3' ends of the same cloned fragment, respectively), H05134 and H05177 (3' and 5' ends of the same cloned fragment, respectively), HSC1WF112 and HSC1WF111 (3' and 5' ends of the same cloned fragment, respectively), T81481 and T81690 (3' and 5' ends of the same cloned fragment, respectively), R77495 (a 3' end of a cloned fragment), and T84377 and T89295 (5' and 3' ends of the same cloned fragment, respectively).

FIG. 4 discloses an alignment of VH1.4 (top) with 11 EST cDNA sequences from GenBank. It is noted that the 3' EST's are at the polyA end and that the EST's cover only a little more than half of the full-length sequence of VH1.4.

EXAMPLE 4

Receptor IgG Precipitation of $^{35}$S-Labeled VRP

To determine whether VRP is a ligand for Flt4, expression plasmids containing the VH1.4 cDNA clone, as well as control plasmids (the expression vector alone or with VEGF or PlGF DNA), were transfected into COS7 cells and the proteins labeled with $^{35}$S amino acids. Conditioned media from these cells was precipatated with Flt4/IgG and Flk1/IgG. Specifically, the VRP expression plasmid, pRK.vh1.4.2, was constructed by deleting about 360 bp of 5' untranslated sequence (5' of the AgeI site (FIG. 3A) from VH1.4). This DNA and control plasmids encoding $VEGF_{165}$ (Houck et al., *Mol. Endocrinol.*, 5: 1806-1814 [1991]), $PlGF_{152}$ (Park et al., supra), or the vector alone (pRK5; Suva et al, supra) were transfected into COS7 cells with DEAE-dextran. Janssen et al., supra. Two days after transfection, the cells were pulse-labeled in 10-cm dishes for 5 hours with 5 mL of methionine- and cysteine-free DMEM supplemented with 100 µCi/mL of $^{35}$S amino acids (Pro-Mix™ brand; Amersham #SJQ0079) at 37° C., and then chased with DMEM for 7 hours. The labeled conditioned medium was concentrated 10-fold by spin concentration (Centricon-10™ brand; Amicon #4203). Fifty µL of the concentrated medium was incubated with 3 µg of receptor IgG and 80 µL of a 50% slurry of protein A agarose (Calbiochem) overnight at 4° C. The precipitates were washed with PBS/0.1% Triton X-100, boiled in SDS sample buffer, and electrophoresed on 12% SDS polyacrylamide gels (Novex #EC60052). The gels were treated with autoradiography enhancer (duPont #NEF974) and exposed overnight at −70° C.

Two specific bands of 53 kDa and 33 kDa were precipitated from the VRP transfection by the Flt4/IgG; these bands were absent in the vector transfection. Little or no specific precipitation of these two bands was found with Flt1/IgG or Flk1/IgG. At times, some VRP precipitation was detected with Flk1/IgG, suggesting that VRP may have a low-affinity interaction with Flk1. Transfection with a VEGF-expressing plasmid showed the expected precipitation of a strong band of about 22 kDa with Flt1/IgG and Flk1/IgG (DeVries et al., supra; Quinn et al., supra; Millauer et al., supra; Terman et al., *Biochem. Biophys. Res. Commun.*, supra), but no precipitation with Flt4/IgG. Similar experiments with labeled PlGF showed no precipitation by Flt4/IgG, but did give the expected precipitation by Flt1/IgG, but not by Flk1/IgG. Park et al., supra. These data indicate that the VRP binds to the extracellular domain of the Flt4 receptor, but does not interact (or does so much more weakly) with the VEGF receptors Flt1 or Flk1. They also confirm the lack of an interaction of VEGF with Flt4 (Pajusola et al., *Oncogene*, 9, supra) and indicate that PlGF is also not a ligand for this receptor.

EXAMPLE 5

Tyrosine Phosphorylation of Flt4 Receptor

To assay Flt4 tyrosine phosphorylation (also described in PCT/US93/00586, supra), Flt4 was expressed in 293 cells and Flt4 phosphorylation monitored by phosphotyrosine immunoblot. Specifically, DNA encoding the long form of human Flt4 was cloned into the mammalian expression vector pRK5 (Suva et al., supra) to give the plasmid pRK.tk1-3.1. This plasmid was co-transfected with a plasmid containing a miroglycoside phosphotransferase (neo) transcription unit into 293 cells by calcium phosphate precipitation (Janssen et al., supra), and stably transfected lines were selected by growth on G418 (Gibco).

One clonal cell line expressing Flt4 (clone 31), as determined by FACS analysis with Flt4/IgG antiserum, and untransfected 293 cells were used in the Flt4 tyrosine phosphorylation assays. One million cells in 100 µL of PBS/0.1% bovine serum albumin (BSA) were mixed with 100 µL of sample and incubated at 37° C. for 15 minutes. The cells were then collected by centrifugation and lysed in 250 µL of 0.15 M NaCl, 10% glycerol, 1% Triton X-100, 50 mM HEPES pH 7.3, 4 µg/mL PMSF, 0.02 u/mL aprotinin (Sigma A6279), and 20 mM sodium orthovanadate. Flt4 was immunoprecipitated by the addition of 8 µL of rabbit Flt4/IgG antiserum and 30 µL of protein A agarose. Washed precipitates were boiled in SDS sample buffer, electrophoresed on polyacrylamide gels (Novex), transferred to nitrocellulose (Janssen et al., supra), and probed with an anti-phosphotyrosine monoclonal antibody (Upstate Biotechnology) and an alkaline phosphatase detection system (Promega).

Samples containing VRP or VEGF were prepared by the electroporation of expression plasmids encoding VH1.4 (pRK.vh1.4.2) or VEGF (Houck et al., supra) into 293 cells and 20-fold concentration (Centricon-10, Amicon) of the 3-day serum-free conditioned medium. In the receptor IgG competition experiments, the concentrated conditioned media were pre-incubated 1 hour at 4° C. with receptor IgG.

Without stimulation, 293 cells expressing or not expressing Flt4 showed little or no Flt4 tyrosine phosphorylation. Stimulation of the Flt4-expressing cells by Flt4/IgG antiserum showed the tyrosine phosphorylation of two bands of 180 and 120 kDa. No increase above basal phosphorylation was observed with preimmune serum, and no bands were found with Flt4/IgG antiserum stimulation of non-expressing cells. Two Flt4 bands of about this size have been reported as being expressed by DAMI and HEL cells. Pajusola et al., *Oncogene*, 8, supra. In addition, SDS gel analysis of purified Flt4/IgG shows that it is composed of peptides of 150, 80, and 70 kDa. N-terminal amino acid sequence of the Flt4/IG peptides shows that the 150 and 70 kDa bands have the amino acid sequence YSMTPPTL (SEQ ID NO: 9) (matching the Flt4 sequence starting at residue 25) and that the 80 kDa band has the sequence SLRRRQQQD (SEQ ID NO: 10) (matching the Flt4 sequence beginning at residue 473). Thus, both the Flt4/IgG and full-length Flt4 appear to be partially cleaved in the extracellular domain, and the tyrosine phosphorylated bands of 180 and 120 kDa observed in the Flt4 phosphorylation assays would correspond to the 150 and 80 kDa peptides of Flt4/IgG. Addition of a polyclonal antiserum to the Flt4 expressing cells showed the tyrosine phosphorylation of two Flt4 bands of 180 and 120 kDa; no bands were observed in non-expressing cells. These data show that polyclonal antibodies generated to the extracellular domain of the Flt4 receptor are capable of activating Flt4 tyrosine phosphorylation.

To determine whether VRP could activate the tyrosine phosphorylation of Flt4, conditioned media from mammalian cells transfected with the VRP expression plasmid was assayed. This conditioned medium stimulated the tyrosine phosphorylation of the same 180 and 120 kDa bands found with the agonist polyclonal antibodies, demonstrating that VRP is able to stimulate the phosphorylation of, as well as bind to, Flt4. Conditioned medium from VEGF-expressing cells failed to activate Flt4 tyrosine phosphorylation.

To confirm the specificity of VRP binding to the receptors of the VEGF family, Flt4/IgG, Flt1/IgG, Flk1/IgG, and Htk/IgG were tested for their ability to compete for VRP-stimulated Flt4 phosphorylation. As expected if VRP is a ligand for Flt4, Flt4/IgG prevented the VRP-stimulated phosphorylation, while Flt1/IgG, Flk1/IgG, and Htk/IgG, a fusion protein from an unrelated tyrosine kinase receptor, had little or no effect. These data show that VRP is able to induce the tyrosine phosphorylation of Flt4.

EXAMPLE 6

Purification of VRP and Binding to Labeled Flt4/IgG

The reading frame encoding the N-terminal secretion signal sequence and about 30 amino acids of the herpes glycoprotein D (Lasky and Dowbenko, *DNA*, 3: 23-29 [1984]; Pennica et al., *Proc. Natl. Acad. Sci. USA*, 92: 1142-1146 [1995]) were fused with a short linker sequence to the putative mature sequence of VRP. Following secretion from mammalian cells, this construct is expected to give the N-terminal glycoprotein D sequence: KYALADASLKMADPNR-FRGKDLPVLDQLLEGGAAHYALLP (SEQ ID NO: 11) followed by the mature VRP sequence GPREAPAAAAAFE (SEQ ID NO: 12). DNA encoding this fusion protein was cloned into the vector pRK5 to give the plasmid pRK.vh1.4.5. This plasmid was transfected into 293 cells by electroporation (Janssen et al., supra), and VRP purified from the 3-4 day serum-free conditioned medium by monoclonal antibody (5B6) affinity chromatography and quantitated by calorimetric assay (Bio-Rad). This antibody is specific for the glycoprotein D sequence fused to the N-terminus of VRP.

Flt4/IgG was iodinated to a specific activity of 1000-1500 Ci/mmol with Iodobeads™ brand iodinated beads (Pierce). Binding was performed with ~20,000 cpm $^{125}$I-Flt4/IgG and 12 ng VH1.4 gD fusion protein in PBS, 0.5% BSA, 0.02% Tween-20™ surfactant, 1 µg/mL heparin (binding buffer) containing 20 µL of a 50% slurry of glass beads conjugated to ~30 µg anti-gD monoclonal antibody (5B6) in a final volume of 100 µL for 4-6 hours at 22° C. Beads were collected by filtration (Millipore Multiscreen-HV), washed five times with 200 µL binding buffer, and counted. For binding at increasing concentrations of Flt4/IgG (FIG. 5B) the binding buffer was DMEM (low glucose):F12 (50:50), 20 mM sodium HEPES, pH 7.2, 10% fetal bovine serum, 0.2% gelatin, and 1 µg/mL heparin.

Figure 5A:
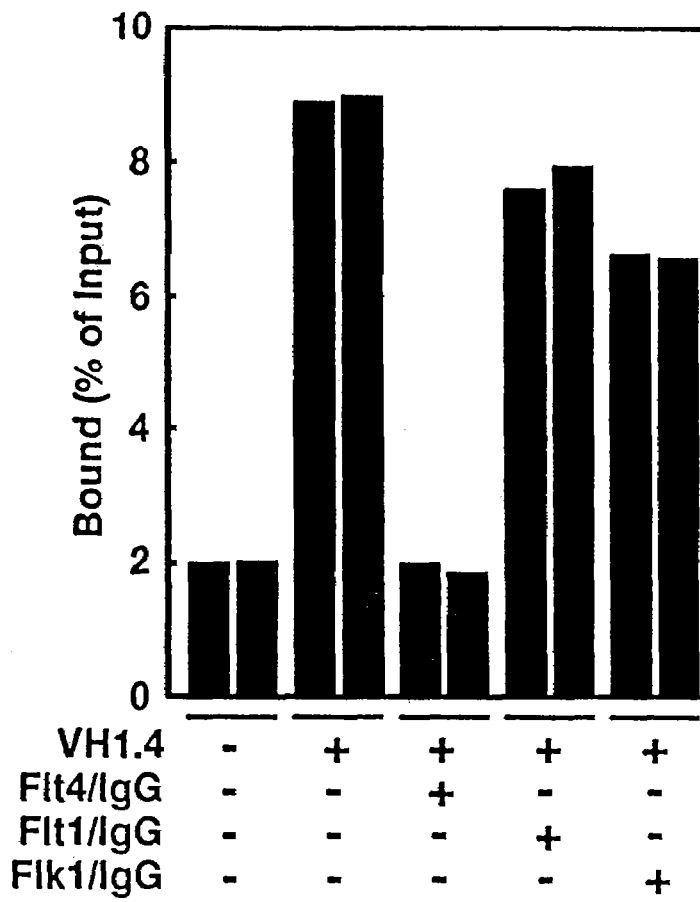
FIG. 5 depicts binding of $^{125}$I-Flt4/IgG to purified VRP. The binding was performed in the absence (−) or presence (+) of 100 nM receptor IgG fusion protein (FIG. 5A) or with increasing concentrations of Flt4/IgG (FIG. 5B).
Figure 5B:
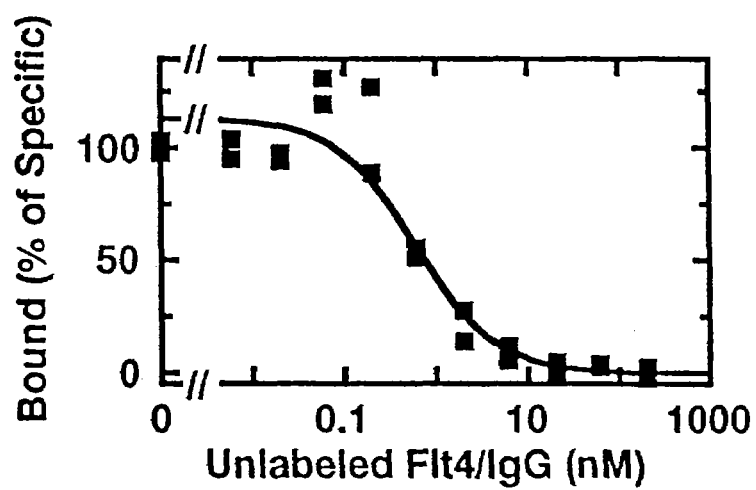

The purified VRP specifically bound to $^{125}$I-Flt4/IgG, and the binding was not competed by unlabeled Flt1/IgG or Flk1/IgG (FIG. 5A). Binding competition with increasing concentrations of unlabeled Flt4/IgG (FIG. 5B) gave an $EC_{50}$ for this interaction of ~0.7 nM, suggesting that the binding of VRP to Flt4 is of high affinity as would be expected if VRP is a biologically relevant ligand for Flt4.

RNA Blots

Blots containing poly(A)+ human RNA were from Clontech. For the G61 glioma cell line, 5 µg of poly(A)+ and poly(A)− RNA were electrophoresed on a 1% agarose/2.2 M formaldehyde gel and transferred to nitrocellulose (Janssen et al., supra). Blots were hybridized with $^{32}$P-labeled probes ovh1.4 and ovh1.5 and washed in 30 mM NaCl/3 mM trisodium citrate at 55° C.

The G61 glioma cell line used in the cloning of VRP expresses a major VRP RNA band of about 2.4 kb. A minor band of about 2.2 kb may also be present. A 2.4 kb band was expressed in adult human tissues from heart, placenta, ovary, and small intestine; a weaker band was found in lung, skeletal muscle, spleen, prostrate, testis, and colon. Expression of a 2.4 kb mRNA was also found in fetal lung and kidney.

EXAMPLE 7

Mitogenic Activity of VRP

Figure 6:
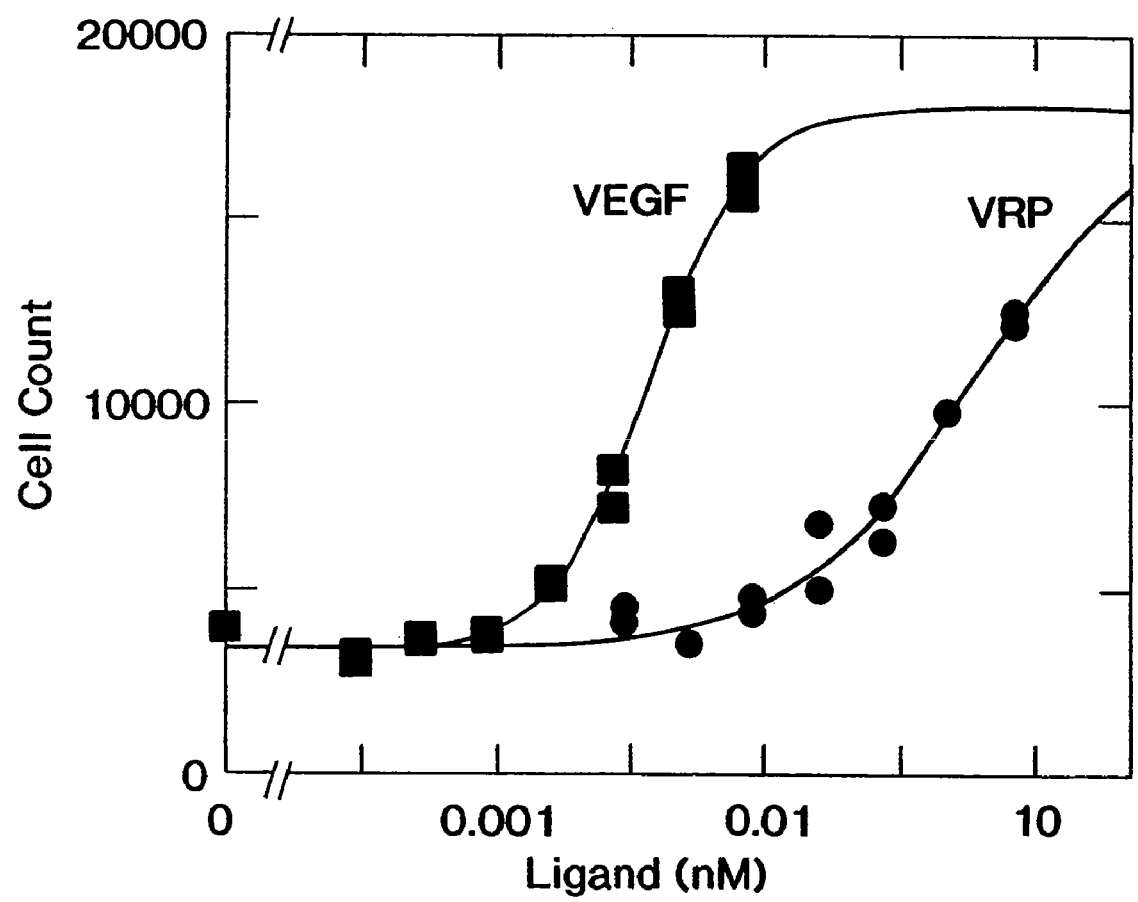
FIG. 6 shows a graph of the cell count of human lung microvascular endothelial cells as a function of the concentration of VEGF or VRP in the cell culture medium to assess and compare mitogenic activity.

To test whether VRP has mitogenic activity like that found for VEGF, the growth of human lung endothelial cells was determined at increasing concentrations of VRP or VEGF (FIG. 6). Specifically, human lung microvascular endothelial cells (HMVEC-L, Clonetics, San Diego, Calif.) were maintained in the recommended growth medium (EGM-MV with 5% fetal calf serum). For the assay of mitogenesis, low passage (<6) cells were seeded at 6500 cells/well in 48-well plates (Costar) and maintained overnight in the recommended growth medium. The medium was removed, and the cells were maintained in the growth medium (2% fetal calf serum) without bovine brain extract and supplemented with VEGF or VRP. After four days, the cells were removed with trypsin and counted with a Coulter counter (Hialeah, Fla.).

VRP promoted the growth of these endothelial cells (see FIG. 6), and thus shares this mitogenic activity with VEGF. This is in contrast to PlGF, which has been reported to lack such mitogenic activity (at ≦35 nM). Park et al., supra. While an effective mitogenic agent, VRP was about 100 fold less potent than VEGF in this assay.

In conclusion, a novel secreted protein, VRP, has now been identified that is a Flt4 ligand and that stimulates the tyrosine phosphorylation of the receptor tyrosine kinase Flt4. VRP is a third member of the VEGF protein family and has about 30% amino acid identity with VEGF and PlGF. In addition to the VEGF-like domain, VRP contains a ~180 amino acid C-terminal, cysteine-rich domain not found in other members of the VEGF family. VRP fails to interact appreciably with the VEGF receptors Flt1 and Flk1.

Deposit of Material

The following plasmid has been deposited with the American Type Culture Collection, 12301 Parklawn Drive, Rockville, Md., USA (ATCC):

| Plasmid | ATCC Dep. No. | Deposit Date |
|---|---|---|
| pRK.vh1.4.1 | 97249 | Sep. 6, 1995 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the plasmid on deposit should die or be lost or destroyed when cultivated under suitable conditions, the plasmid will be promptly replaced on notification with another of the same plasmid. Availability of the deposited plasmid is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule encoding a VEGF-related protein (VRP), wherein said VRP comprises an amino acid sequence selected from the group consisting of residues −20 to 399 of FIG. 1 (residues 1 to 419 of SEQ ID NO:3) and residues 1 to 399 of FIG. 1 (residues 21 to 419 of SEQ ID NO:3).

2. An expression vector comprising the nucleic acid molecule of claim 1.

3. A process for preparing a VRP polypeptide, comprising culturing a host cell transformed with the vector of claim 2 under conditions promoting expression of VRP and recovering the VRP polypeptide.

4. An isolated nucleic acid molecule comprising a nucleotide sequence selected from the group consisting of nucleotides 372 to 1628 of SEQ ID NO:1 and nucleotides 432 to 1628 of SEQ ID NO:1.

5. An expression vector comprising the nucleic acid molecule of claim 4.

6. A process for preparing a VRP polypeptide, comprising culturing a host cell transformed with the vector of claim 5 under conditions promoting expression of VRP and recovering the VRP polypeptide.

7. An isolated nucleic acid molecule encoding a VRP polypeptide, wherein said nucleic acid molecule comprises the VRP cDNA insert of vector deposited in strain ATCC 97249.

8. An expression vector comprising the nucleic acid molecule of claim 7.

9. A process for preparing a VRP polypeptide, comprising culturing a host cell transformed with a vector of claim 8 under conditions promoting expression of VRP polypeptide.

* * * * *

UNITED STATES PATENT AND TRADEMARK OFFICE
CERTIFICATE OF CORRECTION

PATENT NO. : 7,629,145 B2  Page 1 of 1
APPLICATION NO. : 11/427463
DATED : December 8, 2009
INVENTOR(S) : Lee et al.

It is certified that error appears in the above-identified patent and that said Letters Patent is hereby corrected as shown below:

In column 51, under SEQ ID NO:3, at position 114, please delete "Thr" and insert --Tyr--.

Signed and Sealed this

Sixteenth Day of March, 2010

David J. Kappos
*Director of the United States Patent and Trademark Office*